(12) United States Patent
Issa et al.

(10) Patent No.: US 12,018,330 B2
(45) Date of Patent: Jun. 25, 2024

(54) HYPOMETHYLATION OF TET2 TARGET GENES FOR IDENTIFYING A CURABLE SUBGROUP OF ACUTE MYELOID LEUKEMIA

(71) Applicant: Temple University—Of The Commonwealth System of Higher Education, Philadelphia, PA (US)

(72) Inventors: Jean-Pierre J. Issa, Philadelphia, PA (US); Jumpei Yamazaki, Philadelphia, PA (US)

(73) Assignee: Temple University—Of The Commonwealth System of Higher Education, Philadelphia, PA (US)

(*) Notice: Subject to any disclaimer, the term of this patent is extended or adjusted under 35 U.S.C. 154(b) by 224 days.

(21) Appl. No.: 15/769,157

(22) PCT Filed: Oct. 19, 2016

(86) PCT No.: PCT/US2016/057670
§ 371 (c)(1),
(2) Date: Apr. 18, 2018

(87) PCT Pub. No.: WO2017/070189
PCT Pub. Date: Apr. 27, 2017

(65) Prior Publication Data
US 2018/0312927 A1     Nov. 1, 2018

Related U.S. Application Data

(60) Provisional application No. 62/243,231, filed on Oct. 19, 2015.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57426* (2013.01); *C12Q 2600/106* (2013.01); *C12Q 2600/154* (2013.01); *G01N 2800/52* (2013.01)

(58) Field of Classification Search
CPC .................. C12Q 1/6886; C12Q 2600/154
See application file for complete search history.

(56) References Cited

U.S. PATENT DOCUMENTS

| 2009/0264306 A1 | 10/2009 | Caldwell |
| 2009/0317801 A1 | 12/2009 | Van Den Boom |
| 2011/0263523 A1 | 10/2011 | Viguie |

OTHER PUBLICATIONS

Deneberg, S. et al. Leukemia 24:932-941. (Year: 2010).*
Rasmussen et al., "Loss of TET2 in hematopoietic cells leads to DNA hypermethylation of active enhancers and induction of leukemogenesis", Genes & Development, (Apr. 17, 2015), vol. 29, No. 9, pp. 910-922, XP055377038.
Shih et al., "Mutational cooperativity linked to combinatorial epinenetic gain of function in acute myeloid leukemia", Cancer Cell, (Apr. 13, 2015), vol. 27, No. 4, pp. 502-515, XP055377041.

(Continued)

*Primary Examiner* — Diana B Johannsen
(74) *Attorney, Agent, or Firm* — Riverside Law LLP

(57) ABSTRACT

The invention provides AML-specific methylation biomarkers (SP140, MCCC1, EHMT1 and MTSS1). In one embodiment, a biomarker is differentially methylated, specifically in AML.

9 Claims, 33 Drawing Sheets

Specification includes a Sequence Listing.

(56) References Cited

OTHER PUBLICATIONS

Becker et al., "Favorable Prognostic Impact of NPM1 Mutations in Older Patients With Cytogenetically Normal De Novo Acute Myeloid Leukemia and Associated Gene- and MicroRNA-Expression Signatures: A Cancer and Leukemia Group B Study", Journal of Clinical Oncology, vol. 28, No. 4 (2010): 596-604.

Bullinger et al., "Quantitative DNA methylation predicts survival in adult acute myeloid leukemia", Blood, 2010;115:636-642.

Deneberg, "Gene-specific and global methylation patterns predict outcome in patients with acute myeloid leukemia", Leukemia (2010) 24, 932-941.

Figueroa et al., "DNA Methylation Signatures Identify Biologically Distinct Subtypes in Acute Myeloid Leukemia", Cancer Cell, 2010; 17(1): 13-27.

Green et al., "Prognostic Significance of CEBPA Mutations in a Large Cohort of Younger Adult Patients With Acute Myeloid Leukemia: Impact of Double CEBPA Mutations and the Interaction With FLT3 and NPM1 Mutations", J Clin Oncol., vol. 28:2739-2747 (2010).

Jelinek et al., "Conserved DNA methylation patterns in healthy blood cells and extensive changes in leukemia measured by a new quantitative technique", Epigenetics, 7:12, 1368-1378; Dec. 2012.

Ley et al., "DNMT3A Mutations in Acute Myeloid Leukemia", N Engl J Med., (2010); 363(25): 2424-2433.

Marcucci et al., "IDH1 and IDH2 Gene Mutations Identify Novel Molecular Subsets Within De Novo Cytogenetically Normal Acute Myeloid Leukemia: A Cancer and Leukemia Group B Study", J Clin Oncol., vol. 28:2348-2355 (2010).

Mardis et al., "Recurring Mutations Found by Sequencing an Acute Myeloid Leukemia Genome", N Engl J Med., (2009); 361(11): 1058-1066.

Preudhomme et al., "Favorable prognostic significance of CEBPA mutations in patients with de novo acute myeloid leukemia: a study from the Acute Leukemia French Association (ALFA)", Blood, 2002;100:2717-2723.

Walter et al., "Recurrent DNMT3A Mutations in Patients with Myelodysplastic Syndromes", Leukemia, (2011); 25(7): 1153-1158.

Yamazaki et al., "Effects of TET2 mutations on DNA methylation in chronic myelomonocytic leukemia", Epigenetics, vol. 7:2, 201-207; (Feb. 2012).

\* cited by examiner

| Patient characteristics | Test | Validation | TCGA | P value (Test vs Validation) | P value (Test vs TCGA) | P value (Validation vs TCGA) |
|---|---|---|---|---|---|---|
| Total number | 94 | 92 | 194 | | | |
| Age, years | | | | | | |
| Mean | 49 | 50 | 55 | 0.59 | 0.0002 | 0.0007 |
| (Range) | (18-73) | (17-66) | (18-88) | | | |
| Gender | | | | | | |
| Male – no. (%) | 48 (51) | 38 (41) | 54 (28) | 0.19 | 0.71 | 0.06 |
| Bone marrow blasts at diagnosis (%) | | | | 0.24 | <0.0001 | <0.0001 |
| Mean | 58 | 53 | 54 | | | |
| (Range) | (8-96) | (10-99) | (0-98) | | | |
| WBC at diagnosis (*10⁹/dL) | | | | | | |
| Mean | 34 | 15 | 38 | 0.01 | 0.18 | <0.0001 |
| (Range) | (1-228) | (1-162) | (1-298) | | | |
| Cytogenetic risk group – no. (%) | | | | 0.13 | <0.0001 | <0.0001 |
| Favorable | 3 (3) | 0 (0) | 36 (19) | | | |
| Intermediate | 50 (55) | 58 (64) | 113 (59) | | | |
| Poor | 38 (42) | 32 (36) | 42 (22) | | | |
| Antecedent hematologic disorder – no. (%) | 29 (31) | 9 (10) | NA | 0.0005 | NA | NA |
| Complete remission rate – no. (%) | 69 (73) | 72 (78) | NA | 0.5 | NA | NA |
| Overall survival (months) | | | | | | |
| Median | 17 | 19 | 12 | 0.98 | 0.002 | 0.002 |
| (Range) | (0-72+) | (0-82+) | (0-95+) | | | |
| Mutations – no. (%) | | | | | | |
| FLT3-ITD | 22 (24) | 12 (14) | 57 (30) | 0.09 | 0.26 | 0.003 |
| FLT3-TKD | 8 (9) | 5 (6) | NA | 0.57 | NA | NA |
| RAS | 12 (14) | 10 (13) | 11 (6) | 0.82 | 0.03 | 0.08 |
| NPM1 | 21 (24) | 12 (18) | 45 (24) | 0.43 | 1 | 0.39 |
| IDH1 | 3 (3) | 5 (5) | 17 (9) | 0.72 | 0.13 | 0.48 |
| IDH2 | 8 (9) | 5 (6) | 17 (9) | 0.57 | 1 | 0.48 |
| IDH1/2 | 10 (11) | 10 (12) | 34 (18) | 0.82 | 0.16 | 0.28 |
| DNMT3A | 9 (10) | 12 (13) | 18 (25) | 0.64 | 0.02 | 0.07 |

Figure 1

| Patient Characteristics for tet2-DMC-low and high | | | |
|---|---|---|---|
| | tet2-DMC-Low | tet2-DMC-High | P value |
| Total number | 56 | 130 | |
| Age, years | | | |
| Mean | 50 | 49 | 0.96 |
| (Range) | (19-68) | (17-73) | |
| Gender | | | |
| Male – no. (%) | 22 (39) | 64 (49) | 0.26 |
| Bone marrow blasts at diagnosis (%) | | | 0.32 |
| Mean | 53 | 57 | |
| (Range) | (8-96) | (10-99) | |
| WBC at diagnosis (*10³/uL) | | | |
| Mean | 22 | 26 | 0.71 |
| (Range) | (1-148) | (1-228) | |
| Cytogenetic risk group – no. (%) | | | 0.34 |
| Favorable | 2 (4) | 1 (1) | |
| Intermediate | 31 (55) | 77 (62) | |
| Poor | 23 (41) | 47 (38) | |
| Antecedent hematologic disorder – no. (%) | 13 (23) | 25 (19) | 0.56 |
| Complete remission rate – no. (%) | 46 (82) | 95 (73) | 0.2 |
| Overall survival (months) | | | |
| Median | 74+ | 14 | 0.0004 |
| (Range) | (0-79+) | (0-82+) | |
| Mutations – no. (%) | | | |
| FLT3-ITD | 9 (17) | 25 (20) | 0.68 |
| FLT3-TKD | 3 (6) | 10 (8) | 0.76 |
| RAS | 5 (10) | 17 (15) | 0.46 |
| NPM1 | 13 (28) | 20 (19) | 0.21 |
| IDH1 | 2 (4) | 6 (5) | 1 |
| IDH2 | 3 (6) | 10 (8) | 0.76 |
| IDH1/2 | 5 (9) | 15 (12) | 0.8 |
| DNMT3A | 7 (13) | 14 (11) | 0.8 |

Figure 2

Regimens used in the 2 cohorts

| | Test | Validation | Combined |
|---|---|---|---|
| IDA+HIDAC (IA) | 53 | 12 | 65 |
| IA+SAHA | 0 | 43 | 43 |
| IA+ZARNESTRA | 0 | 34 | 34 |
| IA+BAY43-9006 | 40 | 2 | 42 |
| FLAG+MYLO | 1 | 1 | 2 |
| Total | 94 | 92 | 186 |

Figure 17

Primer sequences and PCR conditions

| Gene | Step | Annealing Temp. (°C) | Sequence 5' to 3' | 5'-modified |
|---|---|---|---|---|
| SP140 (hg18, Chr2:230,798,573) | 1 | 58 | AGTTAAGGGAGGAGGAGTAGAGTT (SEQ ID NO:1)<br>CCTTAACAAAAACAAATAACCCTATC (SEQ ID NO:2) | |
| | 2 | 60 | AGTTAAGGGAGGAGGAGTAGAGTT (SEQ ID NO:3)<br>GGGACACCGCTGATCGTTTACCTTAACAAAAACAAATAACCCTATC (SEQ ID NO:4)<br>GGGACACCGCTGATCGTTTA (SEQ ID NO:5) | Biotin |
| | S | | GGAGGAGGAGTAGAGTTAGT (SEQ ID NO:6) | |
| MCCC1 (hg18, Chr3:184,245,211) | 1 | 56 | GAATGATGGTTTGGTTTAGAATGT (SEQ ID NO:7)<br>TCAAATTCACTTCCCCCTAA (SEQ ID NO:8) | |
| | 2 | 58 | GAATGATGGTTTGGTTTAGAATGT (SEQ ID NO:9)<br>GGGACACCGCTGATCGTTTATCAAATTCACTTCCCCCTAA (SEQ ID NO:10)<br>GGGACACCGCTGATCGTTTA (SEQ ID NO:11) | Biotin |
| | S | | AATTTTATTTGTTGGTTGTT (SEQ ID NO:12) | |
| EHMT1 (hg18, Chr9:139,803,373) | 1 | 58 | TGTAAGGGTAGGAGGGGTTGA (SEQ ID NO:13)<br>TTCCCTCCACTCTTAAAACTTTCT (SEQ ID NO:14) | |
| | 2 | 60 | TGTAAGGGTAGGAGGGGTTGA (SEQ ID NO:15)<br>GGGACACCGCTGATCGTTTATTCCCTCCACTCTTAAAACTTTCT (SEQ ID NO:14)<br>GGGACACCGCTGATCGTTTA (SEQ ID NO:15) | Biotin |
| | S | | GTTGTTTTTAGATTTATAT (SEQ ID NO:16) | |
| MTSS1 (hg18, Chr8:125,683,079) | 1 | 56 | AAGTTTTAAATTGGTAGGGGTTTT (SEQ ID NO:17)<br>AATATACCCAACCTTACCCTACTC (SEQ ID NO:18) | |
| | 2 | 58 | AAGTTTTAAATTGGTAGGGGTTTT (SEQ ID NO:19)<br>GGGACACCGCTGATCGTTTAAATATACCCAACCTTACCCTACTC (SEQ ID NO:20)<br>GGGACACCGCTGATCGTTTA (SEQ ID NO:21) | Biotin |
| | S | | GGGGTTTTTTATTTTGA (SEQ ID NO:22) | |
| IDH1 (R132) | 1 | 58 | TGCCAACATGACTTACTTGATCC (SEQ ID NO:23)<br>AATATCCCCCGGCTTGTGA (SEQ ID NO:24) | Biotin |
| | S | | TGATCCCCATAAGCAT (SEQ ID NO:25) | |
| IDH2 (R140) | 1 | 58 | TAGGCGTGGGATGTTTTG (SEQ ID NO:26)<br>CAGAGTTCAAGCTGAAGAAGATGT (SEQ ID NO:27) | Biotin |
| | S | | CCCCCCAGGATGTTC (SEQ ID NO:28) | |
| IDH2 (R172) | 1 | 58 | TGCCCAGGTCAGTGGATC (SEQ ID NO:29)<br>GGAGCCCATCATCTGCAAA (SEQ ID NO:30) | Biotin |
| | S | | TCGGCATGGGCGTGC (SEQ ID NO:31) | |
| DNMT3A (R882) | 1 | 58 | TGTGGTTAGACGGCTTCC (SEQ ID NO:31)<br>GGGACACCGCTGATCGTTTAGAAGAGGTGGCGGATGA (SEQ ID NO:32)<br>GGGACACCGCTGATCGTTTA (SEQ ID NO:33) | Biotin |
| | S | | TGACGTCTCCAACATGA (SEQ ID NO:34) | |

Figure 18

Correlations of tet2-DMRs

| | Test | | | | | Validation | | | | | Combined | | | | |
|---|---|---|---|---|---|---|---|---|---|---|---|---|---|---|---|
| R value | MCCC1 | SP140 | EHMT1 | MTSS1 | | R value | MCCC1 | SP140 | EHMT1 | MTSS1 | | R value | MCCC1 | SP140 | EHMT1 | MTSS1 |
| MCCC1 | | 0.56 | 0.34 | 0.14 | | MCCC1 | | 0.61 | 0.41 | 0.64 | | MCCC1 | | 0.59 | 0.37 | 0.37 |
| SP140 | | | 0.47 | 0.49 | | SP140 | | | 0.28 | 0.47 | | SP140 | | | 0.37 | 0.46 |
| EHMT1 | | | | 0.61 | | EHMT1 | | | | 0.51 | | EHMT1 | | | | 0.56 |
| MTSS1 | | | | | | MTSS1 | | | | | | MTSS1 | | | | |
| p value | MCCC1 | SP140 | EHMT1 | MTSS1 | | p value | MCCC1 | SP140 | EHMT1 | MTSS1 | | p value | MCCC1 | SP140 | EHMT1 | MTSS1 |
| MCCC1 | | <0.001 | 0.001 | 0.191 | | MCCC1 | | <0.001 | <0.001 | <0.001 | | MCCC1 | | <0.001 | <0.001 | <0.001 |
| SP140 | | | <0.001 | <0.001 | | SP140 | | | 0.008 | <0.001 | | SP140 | | | <0.001 | <0.001 |
| EHMT1 | | | | <0.001 | | EHMT1 | | | | <0.001 | | EHMT1 | | | | <0.001 |
| MTSS1 | | | | | | MTSS1 | | | | | | MTSS1 | | | | |

Figure 19

A Multivariate analysis for the test cohort

| Covariate | p | Hazard ratio (HR) | 95% CI of HR |
|---|---|---|---|
| ELN-Adverse | <0.0001 | 3.40 | 1.93 to 5.98 |
| AHD | 0.0107 | 2.09 | 1.19 to 3.68 |
| tet2-DMR-low | 0.0002 | 0.29 | 0.15 to 0.55 |

B Multivariate analysis for the combined cohort

| Covariate | p | Hazard ratio (HR) | 95% CI of HR |
|---|---|---|---|
| Age | 0.031 | 1.02 | 1.00 to 1.04 |
| ELN-Favorable | <0.0001 | 0.14 | 0.05 to 0.35 |
| ELN-Intermediate-1 | <0.0001 | 0.31 | 0.20 to 0.48 |
| ELN-Intermediate-2 | 0.0014 | 0.44 | 0.26 to 0.72 |
| AHD | 0.012 | 1.84 | 1.14 to 2.96 |
| tet2-DMR-low | 0.0008 | 0.45 | 0.28 to 0.71 |

C Multivariate analysis for the cohort with a clinically applicable tet2-DMR signature

| Covariate | p | Hazard ratio (HR) | 95% CI of HR |
|---|---|---|---|
| Age | 0.02 | 1.02 | 1.00 to 1.04 |
| ELN-Favorable | <0.0001 | 0.11 | 0.04 to 0.27 |
| ELN-Intermediate-1 | <0.0001 | 0.29 | 0.19 to 0.47 |
| ELN-Intermediate-2 | 0.001 | 0.43 | 0.26 to 0.77 |
| tet2-DMR-low | 0.001 | 0.51 | 0.34 to 0.77 |

Figure 20A – Figure 20C

DNA methylation levels of tet2-DMR in patients with genetic alterations

Figure 21

Patient characteristics for tet2-DMR-low and high defined by the clinically applicable thresholds

| | tet2-DMR-Low | tet2-DMR-High | P value |
|---|---|---|---|
| Total number | 67 | 113 | |
| Age, years | | | |
| Mean | 51 | 49 | 0.66 |
| (Range) | (19-68) | (17-73) | |
| Gender: | | | |
| Male – no. (%) | 30 (45) | 55 (49) | 0.65 |
| Bone marrow blasts at diagnosis (%) | | | 0.57 |
| Mean | 53 | 55 | |
| (Range) | (7-94) | (16-99) | |
| WBC at diagnosis (10³/uL) | | | 0.96 |
| Mean | 21 | 26 | |
| (Range) | (1-129) | (1-228) | |
| Cytogenetic risk group – no. (%) | | | 0.07 |
| Favorable | 3 (5) | 0 (0) | |
| Intermediate | 39 (59) | 65 (59) | |
| Poor | 24 (36) | 45 (41) | |
| Antecedent hematologic disorder – no. (%) | 13 (19) | 23 (20) | 1 |
| Complete remission rate – no. (%) | 56 (84) | 78 (69) | 0.03 |
| Overall survival (months) | | | 0.0005 |
| Median | 79+ | 14 | |
| (Range) | (0-79+) | (0-82+) | |
| Mutations – no. (%) | | | |
| FLT3-ITD | 14 (22) | 20 (18) | 0.55 |
| FLT3-TKD | 3 (5) | 10 (9) | 0.38 |
| RAS | 6 (10) | 16 (17) | 0.25 |
| NPM1 | 18 (28) | 17 (18) | 0.22 |
| IDH1 | 2 (3) | 6 (5) | 0.71 |
| IDH2 | 5 (8) | 8 (7) | 1 |
| IDH1/2 | 7 (11) | 13 (12) | 1 |
| DNMT3A | 10 (16) | 10 (9) | 0.22 |

Figure 22

Patient characteristics for tet2-DMR-low and high in the TCGA dataset

| | tet2-DMR-Low | tet2-DMR-High | P value |
|---|---|---|---|
| Total number | 46 | 146 | |
| Age, years | | | |
|    Mean | 49 | 57 | 0.0011 |
|    (Range) | (21-76) | (18-88) | |
| Gender | | | |
|    Male – no. (%) | 25 (52) | 80 (55) | 0.87 |
| Bone marrow blasts at diagnosis (%) | | | |
|    Mean | 30 | 39 | 0.07 |
|    (Range) | (0-94) | (0-98) | |
| WBC at diagnosis (*10³/uL) | | | |
|    Mean | 29 | 41 | 0.16 |
|    (Range) | (1-134) | (1-298) | |
| Cytogenetic risk group – no. (%) | | | |
|    Favorable | 31 (67) | 5 (3) | < 0.0001 |
|    Intermediate | 14 (30) | 99 (68) | |
|    Poor | 1 (2) | 41 (28) | |
| Acute promyelocytic leukemia (M3) – no. (%) | 18 (38) | 1 (1) | < 0.0001 |
| Overall survival (months) | | | |
|    Median | 55 | 15 | 0.0003 |
|    (Range) | (0-95+) | (0-96+) | |
| Mutations – no. (%) | | | |
|    ASXL1 | 0 (0) | 3 (6) | 1 |
|    DNMT3A | 2 (12) | 17 (31) | 0.13 |
|    FLT3-TKD | 17 (35) | 40 (29) | 0.47 |
|    RAS | 2 (4) | 9 (6) | 0.73 |
|    NPM | 8 (17) | 37 (26) | 0.24 |
|    IDH1 | 1 (2) | 17 (12) | 0.08 |
|    IDH2 | 0 (0) | 17 (12) | 0.008 |
|    TET2 | 0 (0) | 8 (15) | 0.18 |
|    TET2/IDH | 1 (2) | 41 (28) | < 0.0001 |

Figure 23

Patient Characteristics for tet2-DMR-high with and without TET2/IDH mutations

|  | With mutations | Without mutations | P value |
|---|---|---|---|
| Age, years |  |  |  |
| Mean | 61 | 60 | 0.52 |
| (Range) | (27-77) | (18-88) |  |
| Gender: |  |  |  |
| Male – no. (%) | 21 (51) | 59 (56) | 0.06 |
| Bone marrow blasts at diagnosis (%) |  |  | 0.32 |
| Mean | 48 | 29 |  |
| (Range) | (0-97) | (0-98) |  |
| WBC at diagnosis (*10$^3$/uL) |  |  |  |
| Mean | 15 | 20 | 0.47 |
| (Range) | (1-172) | (1-298) |  |
| Cytogenetic risk group – no. (%) |  |  | 0.36 |
| Favorable | 0 (0) | 5 (5) |  |
| Intermediate | 29 (73) | 70 (67) |  |
| Poor | 11 (27) | 30 (28) |  |
| Mutations – no. (%) |  |  |  |
| FLT3-TKD | 9 (24) | 31 (31) | 0.53 |
| RAS | 2 (5) | 7 (7) | 1.0 |
| NPM1 | 14 (36) | 23 (22) | 0.13 |
| ASXL1 | 2 (9) | 1 (3) | 0.55 |
| DNMT3A | 6 (28) | 11 (33) | 0.77 |
| CEBPA | 2 (9) | 4 (12) | 1.0 |

Figure 24

```
                            SEQUENCE LISTING

<160> NUMBER OF SEQ ID NOS: 37

<210> SEQ ID NO 1
<211> LENGTH: 24
<212> TYPE: DNA
<213> ORGANISM: Artificial Sequence
<220> FEATURE:
<223> OTHER INFORMATION: chemically synthesized

<400> SEQUENCE: 1
agttaaggga ggaggagtag agtt                                              24

<210> SEQ ID NO 2
<211> LENGTH: 26
<212> TYPE: DNA
<213> ORGANISM: Artificial Sequence
<220> FEATURE:
<223> OTHER INFORMATION: chemically synthesized

<400> SEQUENCE: 2
ccttaacaaa aacaaataac cctatc                                            26

<210> SEQ ID NO 3
<211> LENGTH: 24
<212> TYPE: DNA
<213> ORGANISM: Artificial Sequence
<220> FEATURE:
<223> OTHER INFORMATION: chemically synthesized

<400> SEQUENCE: 3
agttaaggga ggaggagtag agtt                                              24

<210> SEQ ID NO 4
<211> LENGTH: 46
<212> TYPE: DNA
<213> ORGANISM: Artificial Sequence
<220> FEATURE:
<223> OTHER INFORMATION: chemically synthesized

<400> SEQUENCE: 4
gggacaccgc tgatcgttta ccttaacaaa aacaaataac cctatc                      46

<210> SEQ ID NO 5
<211> LENGTH: 20
<212> TYPE: DNA
<213> ORGANISM: Artificial Sequence
<220> FEATURE:
<223> OTHER INFORMATION: chemically synthesized

<400> SEQUENCE: 5
gggacaccgc tgatcgttta                                                   20

<210> SEQ ID NO 6
<211> LENGTH: 20
<212> TYPE: DNA
<213> ORGANISM: Artificial Sequence
<220> FEATURE:
<223> OTHER INFORMATION: chemcially synthesized

<400> SEQUENCE: 6
```
ggaggaggag tagagttagt                                               20

<210> SEQ ID NO 7
<211> LENGTH: 24
<212> TYPE: DNA
<213> ORGANISM: Artificial Sequence
<220> FEATURE:
<223> OTHER INFORMATION: chemcially synthesized

<400> SEQUENCE: 7
gaatgatggt ttggtttaga atgt                                          24

<210> SEQ ID NO 8
<211> LENGTH: 20
<212> TYPE: DNA
<213> ORGANISM: Artificial Sequence
<220> FEATURE:
<223> OTHER INFORMATION: chemically synthesized

<400> SEQUENCE: 8
tcaaattcac ttccccctaa                                               20

<210> SEQ ID NO 9
<211> LENGTH: 24
<212> TYPE: DNA
<213> ORGANISM: Artificial Sequence
<220> FEATURE:
<223> OTHER INFORMATION: chemically synthesized

<400> SEQUENCE: 9
gaatgatggt ttggtttaga atgt                                          24

<210> SEQ ID NO 10
<211> LENGTH: 40
<212> TYPE: DNA
<213> ORGANISM: Artificial Sequence
<220> FEATURE:
<223> OTHER INFORMATION: chemically synthesized

<400> SEQUENCE: 10
gggacaccgc tgatcgttta tcaaattcac ttccccctaa                         40

<210> SEQ ID NO 11
<211> LENGTH: 20
<212> TYPE: DNA
<213> ORGANISM: Artificial Sequence
<220> FEATURE:
<223> OTHER INFORMATION: chemically synthesized

<400> SEQUENCE: 11
gggacaccgc tgatcgttta                                               20

<210> SEQ ID NO 12
<211> LENGTH: 20
<212> TYPE: DNA
<213> ORGANISM: Artificial Sequence
<220> FEATURE:
<223> OTHER INFORMATION: chemically synthesized

<400> SEQUENCE: 12
aattttattt gttggttgtt                                               20

<210> SEQ ID NO 13
<211> LENGTH: 21
<212> TYPE: DNA
<213> ORGANISM: Artificial Sequence

```
<220> FEATURE:
<223> OTHER INFORMATION: chemically synthesized

<400> SEQUENCE: 13
tgtaagggta ggaggggttg a                                              21

<210> SEQ ID NO 14
<211> LENGTH: 24
<212> TYPE: DNA
<213> ORGANISM: Artificial Sequence
<220> FEATURE:
<223> OTHER INFORMATION: chemically synthesized

<400> SEQUENCE: 14
ttccctccac tcttaaaact ttct                                           24

<210> SEQ ID NO 15
<211> LENGTH: 21
<212> TYPE: DNA
<213> ORGANISM: Artificial Sequence
<220> FEATURE:
<223> OTHER INFORMATION: chemically synthesized

<400> SEQUENCE: 15
tgtaagggta ggaggggttg a                                              21

<210> SEQ ID NO 16
<211> LENGTH: 44
<212> TYPE: DNA
<213> ORGANISM: Artificial Sequence
<220> FEATURE:
<223> OTHER INFORMATION: chemically synthesized

<400> SEQUENCE: 16
gggacaccgc tgatcgttta ttccctccac tcttaaaact ttct                     44

<210> SEQ ID NO 17
<211> LENGTH: 20
<212> TYPE: DNA
<213> ORGANISM: Artificial Sequence
<220> FEATURE:
<223> OTHER INFORMATION: chemically synthesized

<400> SEQUENCE: 17
gggacaccgc tgatcgttta                                                20

<210> SEQ ID NO 18
<211> LENGTH: 19
<212> TYPE: DNA
<213> ORGANISM: Artificial Sequence
<220> FEATURE:
<223> OTHER INFORMATION: chemically synthesized

<400> SEQUENCE: 18
gttgttttta gatttatat                                                 19

<210> SEQ ID NO 19
<211> LENGTH: 24
<212> TYPE: DNA
<213> ORGANISM: Artificial Sequence
<220> FEATURE:
<223> OTHER INFORMATION: chemically synthesized

<400> SEQUENCE: 19
aagttttaaa ttggtagggg tttt                                           24
```

<210> SEQ ID NO 20
<211> LENGTH: 24
<212> TYPE: DNA
<213> ORGANISM: Artificial Sequence
<220> FEATURE:
<223> OTHER INFORMATION: chemically synthesized

<400> SEQUENCE: 20 aatatacccca accttaccct actc                                          24

<210> SEQ ID NO 21
<211> LENGTH: 24
<212> TYPE: DNA
<213> ORGANISM: Artificial Sequence
<220> FEATURE:
<223> OTHER INFORMATION: chemically synthesized

<400> SEQUENCE: 21
aagttttaaa ttggtagggg tttt                                           24

<210> SEQ ID NO 22
<211> LENGTH: 44
<212> TYPE: DNA
<213> ORGANISM: Artificial Sequence
<220> FEATURE:
<223> OTHER INFORMATION: chemically synthesized

<400> SEQUENCE: 22
gggacaccgc tgatcgttta aatatacccca accttaccct actc                    44

<210> SEQ ID NO 23
<211> LENGTH: 20
<212> TYPE: DNA
<213> ORGANISM: Artificial Sequence
<220> FEATURE:
<223> OTHER INFORMATION: chemically synthesized

<400> SEQUENCE: 23
gggacaccgc tgatcgttta                                                20

<210> SEQ ID NO 24
<211> LENGTH: 18
<212> TYPE: DNA
<213> ORGANISM: Artificial Sequence
<220> FEATURE:
<223> OTHER INFORMATION: chemically synthesized

<400> SEQUENCE: 24
ggggtttttt tattttga                                                  18

<210> SEQ ID NO 25
<211> LENGTH: 23
<212> TYPE: DNA
<213> ORGANISM: Artificial Sequence
<220> FEATURE:
<223> OTHER INFORMATION: chemically synthesized

<400> SEQUENCE: 25
tgccaacatg acttacttga tcc                                            23

<210> SEQ ID NO 26
<211> LENGTH: 19
<212> TYPE: DNA
<213> ORGANISM: Artificial Sequence
<220> FEATURE:
<223> OTHER INFORMATION: chemically synthesized

```
<400> SEQUENCE: 26
aatatccccc ggcttgtga                                            19

<210> SEQ ID NO 27
<211> LENGTH: 16
<212> TYPE: DNA
<213> ORGANISM: Artificial Sequence
<220> FEATURE:
<223> OTHER INFORMATION: chemically synthesized

<400> SEQUENCE: 27
tgatccccat aagcat                                               16

<210> SEQ ID NO 28
<211> LENGTH: 19
<212> TYPE: DNA
<213> ORGANISM: Artificial Sequence
<220> FEATURE:
<223> OTHER INFORMATION: chemically synthesized

<400> SEQUENCE: 28
taggcgtggg atgtttttg                                            19

<210> SEQ ID NO 29
<211> LENGTH: 24
<212> TYPE: DNA
<213> ORGANISM: Artificial Sequence
<220> FEATURE:
<223> OTHER INFORMATION: chemically synthesized

<400> SEQUENCE: 29
cagagttcaa gctgaagaag atgt                                      24

<210> SEQ ID NO 30
<211> LENGTH: 15
<212> TYPE: DNA
<213> ORGANISM: Artificial Sequence
<220> FEATURE:
<223> OTHER INFORMATION: chemically synthesized

<400> SEQUENCE: 30 cccccccagga tgttc                                               15

<210> SEQ ID NO 31
<211> LENGTH: 18
<212> TYPE: DNA
<213> ORGANISM: Artificial Sequence
<220> FEATURE:
<223> OTHER INFORMATION: chemically synthesized

<400> SEQUENCE: 31
tgcccaggtc agtggatc                                             18

<210> SEQ ID NO 32
<211> LENGTH: 19
<212> TYPE: DNA
<213> ORGANISM: Artificial Sequence
<220> FEATURE:
<223> OTHER INFORMATION: chemically synthesized

<400> SEQUENCE: 32
ggagcccatc atctgcaaa                                            19

<210> SEQ ID NO 33
```

```
<211> LENGTH: 15
<212> TYPE: DNA
<213> ORGANISM: Artificial Sequence
<220> FEATURE:
<223> OTHER INFORMATION: chemically synthesized

<400> SEQUENCE: 33
tcgccatggg cgtgc                                                       15

<210> SEQ ID NO 34
<211> LENGTH: 18
<212> TYPE: DNA
<213> ORGANISM: Artificial Sequence
<220> FEATURE:
<223> OTHER INFORMATION: chemically synthesized

<400> SEQUENCE: 34
tgtggttaga cggcttcc                                                    18

<210> SEQ ID NO 35
<211> LENGTH: 37
<212> TYPE: DNA
<213> ORGANISM: Artificial Sequence
<220> FEATURE:
<223> OTHER INFORMATION: chemically synthesized

<400> SEQUENCE: 35
gggacaccgc tgatcgttta gaagaggtgg cggatga                               37

<210> SEQ ID NO 36
<211> LENGTH: 20
<212> TYPE: DNA
<213> ORGANISM: Artificial Sequence
<220> FEATURE:
<223> OTHER INFORMATION: chemically synthesized

<400> SEQUENCE: 36
gggacaccgc tgatcgttta                                                  20

<210> SEQ ID NO 37
<211> LENGTH: 17
<212> TYPE: DNA
<213> ORGANISM: Artificial Sequence
<220> FEATURE:
<223> OTHER INFORMATION: chemically synthesized

<400> SEQUENCE: 37
tgacgtctcc aacatga                                                     17
```

HYPOMETHYLATION OF TET2 TARGET GENES FOR IDENTIFYING A CURABLE SUBGROUP OF ACUTE MYELOID LEUKEMIA

CROSS-REFERENCE TO RELATED APPLICATIONS

This application is the U.S. national phase application filed under 35 U.S.C. § 371 claiming benefit to International Patent Application No. PCT/US2016/057670, filed on Oct. 19, 2016, which is entitled to priority under 35 U.S.C. § 119(e) to U.S. provisional application No. 62/243,231, filed Oct. 19, 2015, the disclosures of which are incorporated herein by reference in their entirety.

STATEMENT REGARDING FEDERALLY SPONSORED RESEARCH OR DEVELOPMENT

This invention was made with government support under CA121104, and CA100632 awarded by the National Institutes of Health. The Government has certain rights in the invention.

BACKGROUND OF THE INVENTION

Acute myeloid leukemia (AML) is a highly heterogeneous hematologic malignancy. Most genetic and cytogenetic changes in AML have now been identified. Although these genetic changes are useful for classification and prognostication, (Grimwade D, et al.; Blood. 1998; 92(7):2322-2333; Slovak M L, et al.; Blood. 2000; 96(13):4075-4083; and Byrd J C, et al.; Blood. 2002; 100(13):4325-4336) they do not fully explain the clinical heterogeneity in outcomes. About half of patients with AML have an intermediate cytogenetic risk where heterogeneity remains problematic. Recent advances in the treatment for AML have improved outcomes for young patients through chemo-intensification and/or the use of allogeneic bone marrow transplantation (Derolf A R, et al.; Blood. 2009; 113(16):3666-3672) About half of young patients can be cured by chemotherapy alone and identifying this curable subset will facilitate management of AML. Epigenetic mechanisms such as DNA methylation are important in control of gene expression in stem cell physiology, normal differentiation, and cancer development (Meissner A; Nat Biotechnol; 28(10):1079-1088; and Jones P A, et al.; Cell. 2007; 128(4):683-692). DNA methylation is frequently abnormal in AML as examined by studies of individual genes and genome wide (Toyota M, et al.; Blood. 2001; 97(9):2823-2829; Jiang Y, et al.; Blood. 2009; 113(6):1315-1325; Figueroa M E, et al.; Blood. 2009; 114(16):3448-3458; and Figueroa M E, et al.; Cancer Cell. 2010; 18(6):553-567). DNA methylation patterns can also be prognostic in AML, either when studied genome-wide (Figueroa M E, et al.; Cancer Cell. 2010; 17(1):13-27) or in a gene-specific manner (Bullinger L et al.; Blood. 2010; 115(3):636-642; and Deneberg S., et al; Leukemia. 2010; 24(5):932-941). In addition, clinical studies with DNA methyltransferase inhibitors have shown impressive responses in some patients (Pollyea D A, et al.; Haematologica. 2013; 98(4):591-596), suggesting that aberrant DNA methylation may be a hallmark of the disease. Several genes encoding DNA methylation enzymes (DNMT3A) (Ley T J, et al.; N Engl J Med. 2010; 363(25):2424-2433), DNA demethylating enzymes (TET2) Abdel-Wahab O, et al.; Blood. 2009; 114(1):144-147), and related genes (IDH1/2) are mutated in AML (Mardis E R, et al.; N Engl J Med. 2009; 361(11):1058-1066). TET2 and IDH1/2 mutations are potentially important because animal models of these replicate aspects of the human phenotype (Quivoron C., et al.; Cancer Cell. 2011; 20(1):25-38; and Moran-Crusio et al.; Cancer Cell. 2011; 20(1):11-24). TET2, IDH1, IDH2 mutations tend to be mutually exclusive and are thought to cause leukemia by inducing aberrant DNA methylation at specific targets (Figueroa M E, et al.; Cancer Cell. 2010; 18(6):553-567).

The prognostic impact of TET2, IDH1, and IDH2 status has been difficult to ascertain because of contradictory findings in different studies. For example, a bad outcome for TET2 mutations was seen in some studies (Abdel-Wahab O, et al.; Blood. 2009; 114(1):144-147; Nibourel O., et al.; Blood. 2010; 116(7):1132-1135; and Metzeler K H, et al.; J Clin Oncol. 2011; 29(10):1373-1381), whereas no difference was seen in others (Gaidzik V I, et al.; J Clin Oncol. 2012; 30(12):1350-1357; and Itzykson R., et al.; Leukemia. 2011; 25(7):1147-1152). Similarly, IDH mutations were shown to be unfavorable in one study (IDH1) (Schnittger S, et al.; Blood. 2010; 116(25):5486-5496), favorable in one (IDH2), (Patel J P, et al.; N Engl J Med. 2012; 366 (12):1079-1089) and had no effect on survival in others (IDH226 and IDH127).

There is a need in the art for a method capable of identifying a curable subset of AML that cannot otherwise be identified with cytogenetics and genetics alone. The present invention addresses this unmet need.

SUMMARY OF THE INVENTION

In one embodiment, the invention provides a method to determine a course of treatment for a patient with acute myelogenous leukemia (AML). In one embodiment, the method comprises: a) determining the level of methylation of a biomarker in a biological sample of the subject, b) comparing the level of methylation of the biomarker with a comparator control, and c) determining a course of treatment based on whether the level of methylation of the biomarker is higher or lower than the level of methylation of the comparator control.

In one embodiment, the biomarker is TET2-specific differentially methylated regions (tet2-DMCs).

In one embodiment, the biomarker is selected from the group consisting of SP140, MCCC1, EHMT1, and MTSS1, and any combination thereof.

In one embodiment, if the level of methylation of a biomarker is increased relative to the comparator control, the subject is treated with alternative therapies for AML.

In one embodiment, the level of methylation of the biomarker is measured by detecting the methylation of CpG sequences in the promoter, gene or related regulatory sequence of the biomarker.

In one embodiment, the level of methylation of the biomarker is measured by a method selected from the group consisting of PCR, methylation-specific PCR, real-time methylation-specific PCR, PCR assay using a methylation DNA-specific binding protein, quantitative PCR, a DNA chip-based assay, pyrosequencing, and bisulfate pyrosequencing.

In one embodiment, the CpG sequences are located on a region selected from the group consisting of promoter sequences upstream of coding sequences, in the coding regions, in enhancer regions, in intron regions, and any combination thereof.

In one embodiment, the comparator control is the level of the biomarker in a healthy subject.

In one embodiment, the comparator control is at least one selected from the group consisting of a positive control, a negative control, a historical control, a historical norm, or the level of a reference molecule in a biological sample.

In one embodiment, the subject is human.

The invention also provides a kit for determining the course of treatment for acute myelogenous leukemia. In one embodiment, the kit comprises a reagent for measuring the level of methylation of a biomarker in a biological sample of the subject wherein the biomarker is selected from the group consisting of SP140, MCCC1, EHMT1, and MTSS1, and any combination thereof.

In one embodiment, when the level of methylation of a biomarker is increased, the subject is diagnosed with aggressive acute myelogenous leukemia and treated using alternative therapies.

The invention also provides a method of determining a course of treatment for a patient with acute myelogenous leukemia, the method comprising diagnosing acute myelogenous leukemia in a subject and administering an anti-cancer therapy to the subject in need thereof, wherein determining the course of treatment for acute myelogenous leukemia in a subject comprises: a) determining the level of methylation of a biomarker in a biological sample of the subject, b) comparing the level of methylation of the biomarker with a comparator control, and c) diagnosing the subject with acute myelogenous leukemia when the level of methylation of the biomarker is different in a statistically significant amount when compared with the level of methylation of the same biomarker of the comparator control.

In one embodiment, the method further comprises diagnosing the subject with aggressive acute myelogenous leukemia when the level of methylation of a biomarker is increased.

In one embodiment, the biomarker is TET2-specific differentially methylated regions (tet2-DMCs).

In one embodiment, the biomarker is selected from the group consisting of SP140, MCCC1, EHMT1, and MTSS1, and any combination thereof.

In one embodiment, the level of methylation of the biomarker is measured by detecting the methylation of the biomarker comprising detecting the methylation of CpG sequences in the promoter, gene or related regulatory sequence of the biomarker.

In one embodiment, the level of methylation of the biomarker is measured by a method selected from the group consisting of PCR, methylation-specific PCR, real-time methylation-specific PCR, PCR assay using a methylation DNA-specific binding protein, quantitative PCR, DNA chip-based assay, pyrosequencing, and bisulfate pyrosequencing.

In one embodiment, the CpG sequences are located in a region selected from the group consisting of upstream of coding sequences, the promoter sequence, in coding regions, in enhancer regions, in intron regions, and any combination thereof.

In one embodiment, the comparator control is the level of the biomarker in the sample of a healthy subject.

In one embodiment, the comparator control is at least one selected from the group consisting of a positive control, a negative control, a historical norm, or the level of a reference molecule in a biological sample.

In one embodiment, the subject is human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 depicts the clinical characteristics of the test (N=94) and validation (N=92) cohorts.

FIG. 2 depicts the clinical characteristics of the tet2-DMC-low (N=56) and tet2-DMC-high (N=130) cohorts.

FIG. 3, comprising

FIG. 5, comprising

FIG. 8, comprising

FIG. 9, comprising

FIG. 11, comprising

FIG. 13, comprising

FIG. 17 depicts the chemotherapy regimens that patients received.

FIG. 18 depicts the primer sequences and PCR conditions for pyrosequencing.

FIG. 19 depicts the correlations of tet2-DMCs.

FIG. 20, comprising FIGS. 20A-20C, depicts multiple regression analysis results identifying covariates as predictors of overall survival.

FIG. 21 depicts the results of various mutations on DNA methylation status for four tet2-DMCs.

FIG. 22 depicts patient characteristics for tet2-DMC-low and -high defined by clinically applicable thresholds.

FIG. 23 depicts patient characteristics for tet2-DMC-low and -high in The Cancer Genome Atlas dataset.

FIG. 24 depicts patient characteristics for tet2-DMC-high with and without TET2/IDH mutations.

DETAILED DESCRIPTION OF THE INVENTION

Figures 3A, 3B, 3C, 3D:
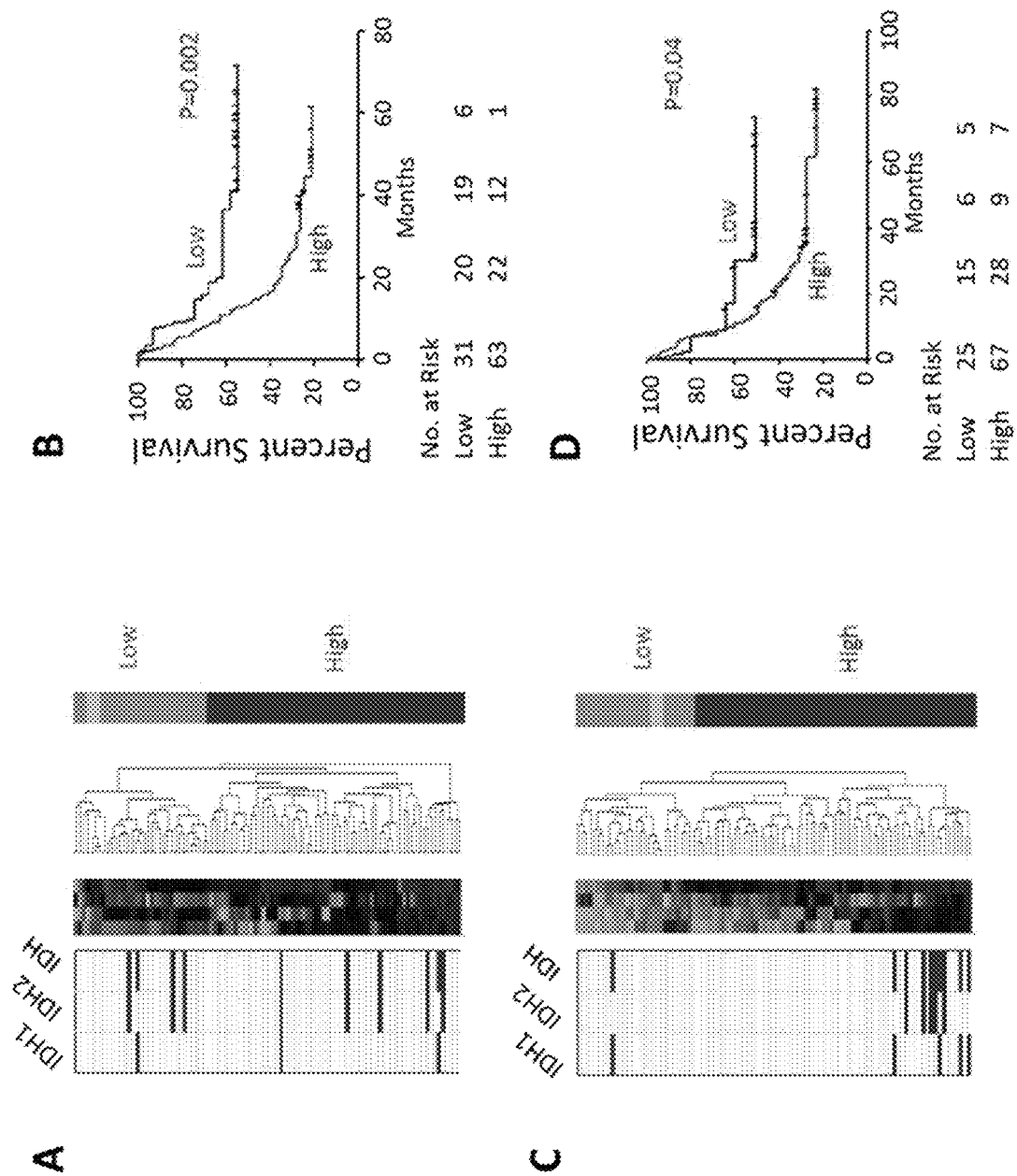
FIGS. 3A-3D, depicts the DNA methylation signatures for tet2-DMC-low and -high patients in AML. Heirarchical clustering analyses (left) in the test cohort (A) and the validation cohort (C) were used for classifying tet2-DMC-low (blue) and -high (red) patients. Note that Normal peripheral blood (green) was clustered with tet2-DMC-low patients. Tet2-DMC-low patients showed significantly longer OS compared to tet2-DMC-high in the test cohort (B) and the validation cohort (D). P values are derived from the log-rank test FIG. 4, comprising

The present invention relates to compositions and methods for AML diagnosis, research and therapy. In particular, the present invention relates to methylation levels of genes as diagnostic markers and clinical targets for AML.

The present invention provides DNA methylation markers associated with AML. Accordingly, a DNA methylation marker associated with AML is considered a biomarker in the context of the present invention.

Accordingly, embodiments of the present invention provide compositions, kits, and methods useful in the detection and screening of AML. Experiments conducted during the course of development of embodiments of the present invention identified methylation status of certain genes in AML. Some embodiments of the present invention provide compositions and methods for detecting such methylated genes. Identification of aberrantly methylated genes is useful in screening, diagnostic and research uses.

In some embodiments, methylation is altered in one or more of the described genes in patients with AML. For example, in some embodiments, methylation of genes is increased relative to a control sample from a subject that does not have AML (e.g., a population average of samples, a control sample, a prior sample from the same patient, etc.). In other embodiments, methylation of genes is decreased relative to a control sample from a subject that does not have AML (e.g., a population average of samples, a control sample, a prior sample from the same patient, etc.). Accordingly, the invention in some instances provides a combination of markers for AML, wherein some of the markers include decreased methylation of a gene and other markers include increased methylation of a gene.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass non-limiting variations of ±40% or ±20% or ±10%, ±5%, ±1%, or ±0.1% from the specified value, as such variations are appropriate.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type, might be abnormal for a different cell or tissue type.

The term "acute myeloid leukemia (AML)", as used herein, refers to a malignant blood disease in which abnormally differentiated myeloid cells reproduce in the bone marrow and spread to the peripheral blood or other organs.

The terms "biomarker" and "marker" are used herein interchangeably. They refer to a substance that is a distinctive indicator of a biological process, biological event and/or pathologic condition.

The term "bisulfite reagent" refers to a reagent comprising bisulfite, disulfite, hydrogen sulfite or combinations thereof, useful as disclosed herein to distinguish between methylated and unmethylated CpG dinucleotide sequences.

The phrase "body sample" or "biological sample" is used herein in its broadest sense. A sample may be of any biological tissue or fluid from which biomarkers of the present invention may be assayed. Examples of such samples include but are not limited to blood, saliva, buccal smear, feces, lymph, urine, gynecological fluids, biopsies, amniotic fluid and smears. Samples that are liquid in nature are referred to herein as "bodily fluids." Body samples may be obtained from a patient by a variety of techniques including, for example, by scraping or swabbing an area or by using a needle to aspirate bodily fluids. Methods for collecting various body samples are well known in the art. Frequently, a sample will be a "clinical sample," i.e., a sample derived from a patient. Such samples include, but are not limited to, bodily fluids which may or may not contain cells, e.g., blood (e.g., whole blood, serum or plasma), urine, saliva, tissue or fine needle biopsy samples, and archival samples with known diagnosis, treatment and/or outcome history. Biological or body samples may also include sections of tissues such as frozen sections taken for histological purposes. The sample also encompasses any material derived by processing a biological or body sample. Derived materials include, but are not limited to, cells (or their progeny) isolated from the sample, proteins or nucleic acid molecules extracted from the sample. Processing of a biological or body sample may involve one or more of: filtration, distillation, extraction, concentration, inactivation of interfering components, addition of reagents, and the like.

In the context of the present invention, the term "control," when used to characterize a subject, refers, by way of non-limiting examples, to a subject that is healthy, to a patient that otherwise has not been diagnosed with a disease. The term "control sample" refers to one, or more than one, sample that has been obtained from a healthy subject or from a non-disease tissue.

The term "control or reference standard" describes a material comprising none, or a normal, low, or high level of one of more of the marker (or biomarker) expression products of one or more the markers (or biomarkers) of the invention, such that the control or reference standard may serve as a comparator against which a sample can be compared.

The term "CpG island" refers to a contiguous region of genomic DNA that satisfies the criteria of a "GC Content">0.5. CpG islands are typically, but not always, between about 0.2 to about 1 kb, or to about 2 kb in length.

"Differentially increased levels" refers to biomarker methylation levels including which are at least 1%, 2%, 3%, 4%, 5%, 10% or more, for example, 5%, 10%, 20%, 30%, 40%, or 50%, 60%, 70%, 80%, 90% higher or more, and/or 0.5 fold, 1.1 fold, 1.2 fold, 1.4 fold, 1.6 fold, 1.8 fold higher or more, as compared with a control.

"Differentially decreased levels" refers to biomarker methylation levels which are at least at least 1%, 2%, 3%, 4%, 5%, 10% or more, for example, 5%, 10%, 20%, 30%, 40%, or 50%, 60%, 70%, 80%, 90% lower or less, and/or 0.9 fold, 0.8 fold, 0.6 fold, 0.4 fold, 0.2 fold, 0.1 fold or less, as compared with a control.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease, or disorder, the frequency with which such a sign or symptom is experienced by a patient, or both, is reduced.

The terms "effective amount" and "pharmaceutically effective amount" refer to a sufficient amount of an agent to provide the desired biological result. That result can be reduction and/or alleviation of a sign, symptom, or cause of a disease or disorder, or any other desired alteration of a biological system. An appropriate effective amount in any individual case may be determined by one of ordinary skill in the art using routine experimentation.

As used herein "endogenous" refers to any material from or produced inside the organism, cell, tissue or system.

"Epigenetic parameters" are, in particular, cytosine methylation. Further epigenetic parameters include, for example, the acetylation of histones which, however, cannot be directly analysed using the described method but which, in turn, correlate with the DNA methylation. As used herein, the term "exogenous" refers to any material introduced from or produced outside the organism, cell, tissue or system.

The term "expression" as used herein is defined as the transcription and/or translation of a particular nucleotide sequence driven by its promoter.

The term "hypermethylation" refers to the average methylation state corresponding to an increased presence of 5-mCyt at one or a plurality of CpG dinucleotides within a DNA sequence of a test DNA sample, relative to the amount of 5-mCyt found at corresponding CpG dinucleotides within a normal control DNA sample.

The term "hypomethylation" refers to the average methylation state corresponding to a decreased presence of 5-mCyt at one or a plurality of CpG dinucleotides within a DNA sequence of a test DNA sample, relative to the amount of 5-mCyt found at corresponding CpG dinucleotides within a normal control DNA sample.

The "level" of one or more biomarkers means the absolute or relative amount or concentration of the biomarker in the sample. The term "level" also refers to the absolute or relative amount of methylation of the biomarker in the sample.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

The term "Methylation assay" refers to any assay for determining the methylation state of one or more CpG dinucleotide sequences within a sequence of DNA.

The term "methylation state" or "methylation status" refers to the presence or absence of 5-methylcytosine ("5-mCyt") at one or a plurality of CpG dinucleotides within a DNA sequence. Methylation states at one or more particular CpG methylation sites (each having two antiparallel CpG dinucleotide sequences) within a DNA sequence include "unmethylated," "fully-methylated" and "hemi-methylated."

The terms "methylation-specific restriction enzymes" or "methylation-sensitive restriction enzymes" shall be taken to mean an enzyme that selectively digests a nucleic acid dependant on the methylation state of its recognition site. In the case of such restriction enzymes which specifically cut if the recognition site is not methylated or hemimethylated, the cut will not take place, or with a significantly reduced efficiency, if the recognition site is methylated. In the case of such restriction enzymes which specifically cut if the recognition site is methylated, the cut will not take place, or with a significantly reduced efficiency if the recognition site is not methylated. Preferred are methylation-specific restriction enzymes, the recognition sequence of which contains a CG dinucleotide (for instance cgcg or cccggg). Further preferred for some embodiments are restriction enzymes that do not cut if the cytosine in this dinucleotide is methylated at the carbon atom C5.

"Non-methylation-specific restriction enzymes" or "non-methylation-sensitive restriction enzymes" are restriction enzymes that cut a nucleic acid sequence irrespective of the methylation state with nearly identical efficiency. They are also called "methylation-unspecific restriction enzymes."

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand that are located 5' to a reference point on the DNA are referred to as "upstream sequences"; sequences on the DNA strand which are 3' to a reference point on the DNA are referred to as "downstream sequences."

The term "pre-cancerous" or "pre-neoplastic" and equivalents thereof shall be taken to mean any cellular proliferative disorder that is undergoing malignant transformation.

As used herein, "predisposition" refers to the property of being susceptible to a cellular proliferative disorder. A subject having a predisposition to a cellular proliferative disorder has no cellular proliferative disorder, but is a subject having an increased likelihood of having a cellular proliferative disorder.

A "polynucleotide" means a single strand or parallel and anti-parallel strands of a nucleic acid. Thus, a polynucleotide may be either a single-stranded or a double-stranded nucleic acid. In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

As used herein, the term "providing a prognosis" refers to providing a prediction of the probable course and outcome of AML, including prediction of severity, duration, chances of recovery, etc. The methods can also be used to devise a suitable therapeutic plan, e.g., by indicating whether or not the condition is still at an early stage or if the condition has advanced to a stage where aggressive therapy would be ineffective.

A "reference level" of a biomarker means a level of the biomarker, for example level of methylation of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype.

By the term "specifically binds," as used herein, is meant a molecule, such as an antibody, which recognizes and binds to another molecule or feature, but does not substantially recognize or bind other molecules or features in a sample.

"Standard control value" as used herein refers to a predetermined methylation level of a biomarker. The standard control value is suitable for the use of a method of the present invention, in order for comparing the amount of methylation of a biomarker of interest that is present in a sample. An established sample serving as a standard control provides an average amount methylation of a biomarker of interest that is typical for an average, healthy person of reasonably matched background, e.g., gender, age, ethnicity, and medical history. A standard control value may vary depending on the biomarker of interest and the nature of the sample.

As used herein, the term "subject" refers to a human or another mammal (e.g., primate, dog, cat, goat, horse, pig, mouse, rat, rabbit, and the like. In many embodiments of the present invention, the subject is a human being. In such embodiments, the subject is often referred to as an "individual" or a "patient." The terms "individual" and "patient" do not denote a particular age.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is bsed on discoverying that low levels of methylation define a curable subset of AML that cannot be identified with cytogenetics and genetics alone.

The present invention is based in part on the discovery that the DNA methylation status of specific regions of SP140, MCCC1, EHMT1, and MTSS1 genes can individually and collectively predict survival after chemotherapy in acute myelogenous leukemia. DNA methylation of these marker genes can significantly discriminate the patients with good or poor survival, independently of any known classification systems currently in use such as clinical characteristics, cytogenetics or mutations in known predictive genes in AML. Patients with high DNA methylation levels of each gene have such poor outcome after standard of care that alternate therapies should be sought for them. Without wishing to be bound by any particular theory, these alternate therapies may include rapid referral for stem cell transplantation, the use of drugs that reduce DNA methylation levels (hypomethylating agents) and/or clinical trials of novel agents used instead of or in addition to chemotherapy. Conversely, patients with low levels of methylation at all genes have a high cure rate with chemotherapy and may be spared the use of risky additional therapies such as stem cell transplantation.

In one embodiment, the invention is based partly on the discovery of four genes that strongly predicted survival in AML (SP140, MCCC1, EHMT1, and MTSS1). SP140 is a component of the nuclear body, which is believed to have function in the pathogenesis of acute promyelocytic leukemia and viral infection. MCCC1 encodes the large subunit of 3-methylcrotonyl-CoA carboxylase. This enzyme functions as a heterodimer and catalyzes the carboxylation of 3-methylcrotonyl-CoA to form 3-methylglutaconyl-CoA. EHMT1 encodes a histone methyltransferase that is part of the E2F6 complex, which represses transcription. The encoded protein methylates the Lys-9 position of histone H3, which tags it for transcriptional repression. This protein is believed to be involved in the silencing of MYC- and E2F-responsive genes and therefore could play a role in the G0/G1 cell cycle transition. MTSS1 is believed to be related to cancer progression or tumor metastasis in a variety of organ sites through an interaction with the actin cytoskeleton. The specific regions analyzed are shown in FIG. 3 and specifically are: 1) SP140: Human genome build hg18, Chr2:230,798,573 (−117 bp from transcription start site (TSS) of SP140); 2) MCCC1: Human genome build hg18, Chr3:184,245,211 (54,848 bp from TSS of MCCC1); 3) EHMT1: Human genome build hg18, Chr9: 139,803,373; and 4) MTSS1: Human genome build hg18, Chr8:125,683,079 (62,555 bp from TSS of MTSS1)

Accordingly, the invention provides AML-specific methylation biomarkers SP140, MCCC1, EHMT1, and MTSS1. In one embodiment, a biomarker is differentially methylated, specifically in AML.

In one embodiment, biomarkers of the invention include one or more of SP140, MCCC1, EHMT1, and MTSS1. In one other embodiment, the present invention includes a method for detecting the methylation of one or more of SP140, MCCC1, EHMT1, and MTSS1, and a kit for determining a course of treatment using the same.

In one embodiment, detection of an increased level of methylation of a biomarker, wherein the biomarker is selected from the group consisting of SP140, MCCC1, EHMT1, and MTSS1, and any combination thereof, is used to identify aggressive AML.

Additional aspects provide novel methods and compositions for determining the relationship between methylation status and other variables including, but not limited to age, sex, preneoplastic state, family history, race, country of origin.

Biomarkers

The present invention provides DNA methylation markers associated with AML. Accordingly, a DNA methylation marker associated with AML is considered a biomarker in the context of the present invention.

A biomarker is an organic biomolecule which is differentially present in a sample taken from an individual of one phenotypic status (e.g., having a disease) as compared with an individual of another phenotypic status (e.g., not having the disease). A biomarker is differentially present between the two individuals if the mean or median expression level, including methylation level, of the biomarker in the different individuals is calculated to be statistically significant. Biomarkers, alone or in combination, provide measures of relative risk that an individual belongs to one phenotypic status or another. Therefore, they are useful as markers for diagnosis of disease, the severity of disease, therapeutic effectiveness of a drug, and drug toxicity.

Accordingly, the invention provides methods for identifying one or more biomarkers that can be used to aid in the diagnosis, detection, and prediction of AML. The methods of the invention are carried out by obtaining a set of measured values for a plurality of biomarkers from a biological sample derived from a test individual, obtaining a set of measured values for a plurality of biomarkers from a biological sample derived from a control individual, comparing the measured values for each biomarker between the test and control sample, and identifying biomarkers which are significantly different between the test value and the control value, also referred to as a reference value.

The process of comparing a measured value and a reference value can be carried out in any convenient manner appropriate to the type of measured value and reference value for the biomarker of the invention. For example, "measuring" can be performed using quantitative or qualitative measurement techniques, and the mode of comparing a measured value and a reference value can vary depending on the measurement technology employed. For example, when a qualitative colorimetric assay is used to measure biomarker levels, the levels may be compared by visually comparing the intensity of the colored reaction product, or by comparing data from densitometric or spectrometric measurements of the colored reaction product (e.g., comparing numerical data or graphical data, such as bar charts, derived from the measuring device). However, it is expected that the measured values used in the methods of the invention will most commonly be quantitative values (e.g., quantitative measurements of concentration). In other examples, measured values are qualitative. As with qualitative measurements, the comparison can be made by inspecting the numerical data, or by inspecting representations of the data (e.g., inspecting graphical representations such as bar or line graphs).

A measured value is generally considered to be substantially equal to or greater than a reference value if it is at least about 95% of the value of the reference value. A measured value is considered less than a reference value if the measured value is less than about 95% of the reference value. A measured value is considered more than a reference value if the measured value is at least more than about 5% greater than the reference value.

The process of comparing may be manual (such as visual inspection by the practitioner of the method) or it may be automated. For example, an assay device (such as a luminometer for measuring chemiluminescent signals) may include circuitry and software enabling it to compare a measured value with a reference value for a desired biomarker. Alternately, a separate device (e.g., a digital computer) may be used to compare the measured value(s) and the reference value(s). Automated devices for comparison may include stored reference values for the biomarker(s) being measured, or they may compare the measured value(s) with reference values that are derived from contemporaneously measured reference samples.

Methylation

In the present invention, any nucleic acid sample, in purified or nonpurified form, can be used, provided it contains or is suspected of containing a nucleic acid sequence containing a target locus (e.g., CpG-containing nucleic acid). One nucleic acid region capable of being differentially methylated is a CpG island, a sequence of nucleic acid with an increased density relative to other nucleic acid regions of the dinucleotide CpG. The CpG doublet occurs in vertebrate DNA at only about 20% of the frequency that would be expected from the proportion of G*C base pairs. In certain regions, the density of CpG doublets reaches the predicted value; it is increased by ten-fold relative to the rest of the genome. CpG islands have an average G*C content of about 60%, compared with the 40% average in bulk DNA. The islands take the form of stretches of DNA typically about one to two kilobases long. There are about 45,000 islands in the human genome.

In many genes, the CpG islands begin just upstream of a promoter and extend downstream into the transcribed region. Methylation of a CpG island at a promoter usually suppresses expression of the gene. The islands can also surround the 5' region of the coding region of the gene as well as the 3' region of the coding region. Thus, CpG islands can be found in multiple regions of a nucleic acid sequence including upstream of coding sequences in a regulatory region including a promoter region, in the coding regions (e.g., exons), downstream of coding regions in, for example, enhancer regions, and in introns. Differential methylation can also occur outside of CpG islands.

Typically, the CpG-containing nucleic acid is DNA. However, the inventive method may employ, for example, samples that contain DNA, or DNA and RNA containing mRNA, wherein DNA or RNA may be single-stranded or double-stranded, or a DNA-RNA hybrid may be included in the sample.

A mixture of nucleic acids may also be used. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. Nucleic acids contained in a sample used for detection of methylated CpG islands may be extracted by a variety of techniques such as that described elsewhere herein or procedures known to those of skill in the art.

In one aspect of the invention, the state of methylation in nucleic acids of the sample obtained from a subject is hypermethylation compared with the same regions of the nucleic acid in a subject not having AML. Hypermethylation as used herein refers to the presence or an increase of methylated alleles in one or more nucleic acids. Nucleic acids from a subject not having AML contain no detectable or lower levels of methylated biomarkers when the same nucleic acids are examined.

It may also be possible for the state of methylation in nucleic acids of the sample obtained from a subject are hypomethylated. Hypomethylation as used herein refers to the absence or diminished level of methylated biomarkers in one or more nucleic acids.

Accordingly, the invention provides markers for aggressive variants of AML, wherein the markers demonstrate increased methylation of a gene.

Detection Methods

In one embodiment, the invention provides diagnostic and screening methods that utilize the detection of aberrant methylation of genes or promoters (e.g., including, but not limited to, SP140, MCCC1, EHMT1, and MTSS1. In some embodiments, methylation of a gene is altered (e.g., increased or decreased). That is, in one embodiment, methylation of a gene is increased relative to a control sample from a subject that does not have AML (e.g., a population average of samples, a control sample, a prior sample from the same patient, etc.) or from a subject that has a more curable form of AML. In some instances the invention provides a combination of markers for aggressive AML, wherein the markers include include increased methylation of a gene.

Any patient sample may be tested according to methods of embodiments of the present invention. In some embodiments, the patient sample is subjected to preliminary processing designed to isolate or enrich the sample for the aberently methylated genes or promoters or cells that contain the aberrantly methylated genes or promoters. A variety of techniques known to those of ordinary skill in the art may be used for this purpose, including but not limited to: centrifugation; immunocapture; cell lysis; and, nucleic acid target capture.

In one embodiment, the biomarkers of the invention can be detected using a pyrosequencing procedure. The pyrosequencing method is a quantitative real-time sequencing method modified from the bisulfite sequencing method. Similarly to bisulfite sequencing, genomic DNA is converted by bisulfite treatment, and then, PCR primers corresponding to a region containing no 5'-CpG-3' base sequence are constructed. Specifically, the genomic DNA is treated with bisulfite, amplified using the PCR primers, and then subjected to real-time base sequence analysis using a sequencing primer. The degree of methylation is expressed as a methylation index by analyzing the amounts of cytosine and thymine in the 5'-CpG-3' region.

In one embodiment, the biomarkers of the invention can be detected using a real-time methylation specific PCR procedure. Real-time methylation-specific PCR is a real-time measurement method modified from the methylation-specific PCR method and comprises treating genomic DNA with bisulfite, designing PCR primers corresponding to the methylated base sequence, and performing real-time PCR using the primers. Methods of detecting the methylation of the genomic DNA include two methods: a method of detection using, for example, a TaqMan™ probe complementary to the amplified base sequence; and a method of detection using Sybergreen™. Thus, the real-time methylation-specific PCR allows selective quantitative analysis of methylated DNA. A standard curve is plotted using an in vitro methylated DNA sample, and a gene containing no 5'-CpG-3' sequence in the base sequence is also amplified as a negative control group for standardization to quantitatively analyze the degree of methylation.

In one embodiment, the biomarkers of the invention can be detected via a PCR using a methylation-specific binding protein or a DNA chip. PCR using a methylation-specific binding protein or a DNA chip assay allows selective isolation of only methylated DNA. Genomic DNA is mixed with a methylation-specific binding protein, and then only methylated DNA was selectively isolated. The isolated DNA is amplified using PCR primers corresponding to the promoter region, and then methylation of the DNA is measured by agarose gel electrophoresis.

In addition, methylation of DNA can also be measured by a quantitative PCR method, and methylated DNA isolated with a methylated DNA-specific binding protein can be labeled with a fluorescent probe and hybridized to a DNA chip containing complementary probes, thereby measuring methylation of the DNA.

In one embodiment, the biomarkers of the invention can be detected by way of using a methylation-sensitive restriction endonuclease. Detection of differential methylation can be accomplished by bringing a nucleic acid sample into contact with a methylation-sensitive restriction endonuclease that cleaves only unmethylated CpG sites. In a separate reaction, the sample is further brought into contact with an isoschizomer of the methylation-sensitive restriction enzyme that cleaves both methylated and unmethylated CpG-sites, thereby cleaving the methylated nucleic acid.

Methylation-sensitive restriction endonucleases can be used to detect methylated CpG dinucleotide motifs. Such endonucleases may either preferentially cleave methylated recognition sites relative to non-methylated recognition sites or preferentially cleave non-methylated relative to methylated recognition sites. Examples of the former are Acc III, Ban I, BstN I, Msp I, and Xma I. Examples of the latter are Acc II, Ava I, BssH II, BstU I, Hpa II, and Not I. Alternatively, chemical reagents can be used which selectively modify either the methylated or non-methylated form of CpG dinucleotide motifs.

Specific primers are added to the nucleic acid sample, and the nucleic acid is amplified by any conventional method. The presence of an amplified product in the sample treated with the methylation-sensitive restriction enzyme but absence of an amplified product in the sample treated with the isoschizomer of the methylation-sensitive restriction enzyme indicates that methylation has occurred at the nucleic acid region assayed. However, the absence of an amplified product in the sample treated with the methylation-sensitive restriction enzyme together with the absence of an amplified product in the sample treated with the isoschizomer of the methylation-sensitive restriction enzyme indicates that no methylation has occurred at the nucleic acid region assayed.

Another method for detecting a methylated CpG-containing nucleic acid comprises the steps of: bringing a nucleic acid-containing sample into contact with an agent that modifies unmethylated cytosine; and amplifying the CpG-containing nucleic acid in the sample using CpG-specific oligonucleotide primers, wherein the oligonucleotide primers distinguish between modified methylated nucleic acid and non-methylated nucleic acid and detect the methylated nucleic acid. The amplification step is optional and desirable, but not essential. The method relies on the PCR reaction to distinguish between modified (e.g., chemically modified) methylated DNA and unmethylated DNA. Such methods are described in U.S. Pat. No. 5,786,146 relating to bisulfate sequencing for detection of methylated nucleic acid.

In another embodiment, the methylation status of the cancer markers may be detected along with other markers in a multiplex or panel format. Markers are selected for their predictive value alone or in combination with the gene fusions.

The methylation levels of non-amplified or amplified nucleic acids can be detected by any conventional means. In other embodiments, the methods described in U.S. Pat. Nos. 7,611,869, 7,553,627, 7,399,614, and/or 7,794,939, each of which is herein incorporated by reference in its entirety, are utilized. Additional detection methods include, but are not limited to, bisulfate modification followed by any number of detection methods (e.g., probe binding, sequencing, amplification, mass spectrometry, antibody binding, a combination of probe binding for sequence capture and subsequent sequencing etc.) methylation-sensitive restriction enzymes and physical separation by methylated DNA-binding proteins or antibodies against methylated DNA (See e.g., Levenson, Expert Rev Mol Diagn. 2010 May; 10(4): 481-488; herein incorporated by reference in its entirety).

In some embodiments, a computer-based analysis program is used to translate the raw data generated by the detection assay (e.g., the presence, absence, or amount of methylation of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine or fecal sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., methylation data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., presence or absence of aberrant methylation) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

Compositions for use in the diagnostic methods described herein include, but are not limited to, probes, amplification oligonucleotides, detection reagents, controls and the like. In some embodiments, reagents are provided in the form of an array.

Diagnostic

In one embodiment, the present invention provides a method to accurately identify known as well as newly discovered diagnostically, prognostically and therapeutically relevant subgroups of acute myeloid leukemia (AML), as well as methods that can predict which approaches in treatment are likely to be effective. The basis of these methods resides in the measurement of methylation status of the markers of the invention. The methods and compositions of the invention thus provide tools useful in choosing a therapy for AML patients, including methods for assigning an AML patient to an AML class or AML cluster, methods of choosing a therapy for an AML patient, methods of determining the efficacy of a therapy in an AML patient, and methods of determining the prognosis for an AML patient.

One aspect of the present invention relates to a method of diagnosing a condition associated with an aberrant methylation of DNA in a sample from a subject by measuring the methylation level of one or more DNA biomarkers from a test sample in comparison to that of a normal or standard sample, wherein the fold difference between the methylation level of the test sample in relation to that of the normal/standard sample indicates the likelihood of the test sample having the condition.

The aberrant methylation is referred as hypermethylation and/or hypomethylation (e.g., demethylation). In a preferred embodiment, the abnormal methylation is hypermethylation. In another preferred embodiment, the abnormal methylation is hypomethylation.

The methylation of DNA often occurs at genome regions known as CpG islands. The CpG islands are susceptible to aberrant methylation (e.g., hypermethylation or hypomethylation) in stage- and tissue-specific manner during the development of a condition or disease (e.g., cancer). Thus the measurement of the level of methylation indicates the likelihood or the stage (e.g., onset, development, or remission stage) of the condition. Accordingly, the invention provides a combination of markers for AML, wherein the markers include increased methylation of a gene.

The methylation of DNA can be detected via methods known in the art and those described elsewhere herein. In one embodiment, the level can be measured via a methylated-CpG island recovery assay (MIRA), combined bisulfite-restriction analysis (COBRA) or methylation-specific PCR (MSP). In another preferred embodiment, the methylation levels of a plurality DNA can be measured through MIRA-assisted DNA array.

The biomarkers are fragments of genome DNA that contain a CpG island or CpG islands, or alternatively, are susceptible to aberrant methylation. Examples of the DNA markers associated with a condition are disclosed elsewhere herein. Specifically, examples of the DNA markers include one or more genes selected from the group consisting of SP140, MCCC1, EHMT1, and MTSS1.

In another embodiment, the method of present invention is directed to a method of diagnosing AML in a test subject or a test sample through determining the methylation level of DNA markers from the test subject or test sample in relative to the level of the DNA markers from a normal subject or sample, wherein the DNA markers are one or more genes selected from the group consisting of SP140, MCCC1, EHMT1, and MTSS1.

It is contemplated that the biomarkers for altered methylation according to the present invention have the following criteria. An altered methylation status that diagnoses aggressive AML can include an increased methylation status relative to a control sample from a subject that does not have AML (e.g., a population average of samples, a control sample, a prior sample from the same patient, etc.) or relative to a threshold value that distinguishes aggressive from chemotherapy-curable AML.

The present invention enables diagnosis of events that are disadvantageous to patients or individuals in which important genetic and/or epigenetic parameters within at least one gene or genomic sequence selected from the group consisting of SP140, MCCC1, EHMT1, and MTSS1, and any combination thereof may be used as markers. The parameters obtained by means of the present invention may be compared to another set of genetic and/or epigenetic parameters, the differences serving as the basis for a diagnosis and/or prognosis of events that are disadvantageous to patients or individuals.

In another embodiment, the present invention enables the differentiation of aggressive forms of AML that are likely to be resistant to standard treatments or relapse following standard treatments from less or non-agressive forms of AML that can be successfully treated using standard treatments.

In one embodiment, the present invention provides for diagnostic and classification of AML based on measurement of differential methylation status of one or more CpG dinucleotide sequences of at least one gene selected from the group consisting of SP140, MCCC1, EHMT1, and MTSS1, and any combination thereof that comprise such a CpG dinucleotide sequence. Typically, such assays involve obtaining a sample from a subject, performing an assay to measure the methylation state of at least one gene or genomic sequence selected from the group consisting of SP140, MCCC1, EHMT1, and MTSS1, and any combination thereof, preferably by determining the methylation status of at least one gene selected from the group consisting of SP140, MCCC1, EHMT1, and MTSS1, and any combination thereof, derived from the sample, relative to a control sample, or a known standard and making a diagnosis based thereon.

Although diagnostic and prognostic accuracy and sensitivity may be achieved by using a combination of markers, such as 2 or more biomarkers of the invention, practical considerations may dictate use of one or more biomarkers and smaller combinations thereof. Any combination of markers may be used which comprises one or all four of the markers diagnosed herein.

The level of methylation of the differentially methylated GpG loci can provide a variety of information about AML. It can be used to predict the course of AML in the individual or to predict the susceptibility to AML or to stage the progression of the AML in the individual. It can help to predict the likelihood of overall survival or predict the likelihood of reoccurrence of AML and to determine the effectiveness of a treatment course undergone by the individual. Increase or decrease of methylation levels in comparison with reference level and alterations in the increase/decrease when detected provides useful prognostic and diagnostic value.

Following the diagnosis of a subject according to the methods of the invention, it is possible to predict whether standard chemotherapy can be used to treat the patient or whether a more aggressive or alternative therapy is needed. Patients with high DNA methylation levels of the biomarkers identifed in the present invention have poor outcomes based on standard care. Accordingly, the method comprises identifying nucleic acid altered methylation (e.g., hypermethylation and/or hypomethylation) of one or more genes, where increased methylation indicates the possibilty for poor survival using only standard chemotherapy.

The prognostic methods can be used to identify patients with aggressive AML. Such patients can be offered additional appropriate therapeutic or preventative options, including personalized medicine based on their genome, bone marrow transplants, surgical procedures, chemotherapy, radiation, biological response modifiers, or other therapies. Such patients may also receive recommendations for further diagnostic or monitoring procedures, including but not limited to increased frequency of checkups.

Therapy

The markers of the invention can be used among other things for the determination of a subject's susceptibility to a disease or disorder, determination as to whether a subject is presently affected by a disease or disorder, prognosis of a subject affected by a disease or disorder (e.g., identification of cancerous states, stages of cancer, or responsiveness of cancer to therapy), and use of therametrics (e.g., monitoring a subject's condition to provide information as to the effect or efficacy of therapy).

The diagnostic methods of the invention also provide for optimizing therapy, by first classification, and based on that information, selecting the appropriate therapy, dose, treatment modality, etc. which optimizes the differential between delivery of an anti-proliferative treatment to the undesirable target cells, while minimizing undesirable toxicity. The treatment is optimized by selection for a treatment that minimizes undesirable toxicity, while providing for effective anti-proliferative activity.

The invention finds use in the prevention, treatment, detection or research of acute myeloid leukemias. Acute leukemias are rapidly progressing leukemia characterized by replacement of normal bone marrow by blast cells of a clone arising from malignant transformation of a hematopoietic stem cell. The acute leukemias include acute lymphoblastic leukemia (ALL) and acute myelogenous leukemia (AML). ALL often involves the CNS, whereas acute monoblastic leukemia involves the gums, and AML involves localized collections in any site (granulocytic sarcomas or chloromas). AML is the most common acute leukemia affecting adults, and its incidence increases with age. While AML is a relatively rare disease overall, accounting for approximately 1.2% of cancer deaths in the United States, its incidence is expected to increase as the population ages.

The invention further provides methods for reducing growth of cancer cells following the diagnosis of AML using the markers of the invention. The methods provide for decreasing the number of cancer cells bearing a specific marker or combination of markers, as provided herein, decreasing expression of a gene that is differentially expressed in a cancer cell, or decreasing the level of and/or decreasing an activity of a cancer-associated polypeptide. In general, the methods comprise contacting a cancer cell with a binding agent, e.g. an antibody or ligand specific for a marker or combination of markers provided herein. In addition, any convention compounds used in the art can be used.

The present invention provides methods for treating cancer, generally comprising administering to an individual in need thereof a substance that reduces cancer cell growth, in an amount sufficient to reduce cancer cell growth and treat the cancer. Whether a substance, or a specific amount of the substance, is effective in treating cancer can be assessed using any of a variety of known diagnostic assays for cancer, including, but not limited to biopsy, contrast radiographic studies, CAT scan, and detection of a tumor marker associated with cancer in the blood of the individual. The substance can be administered systemically or locally, usually systemically.

A substance, e.g. a chemotherapeutic drug that reduces cancer cell growth, can be targeted to a cancer cell. Thus, in some embodiments, the invention provides a method of delivering a drug to a cancer cell, comprising administering a drug-antibody complex to a subject, wherein the antibody is specific for a cancer-associated polypeptide, and the drug is one that reduces cancer cell growth, a variety of which are known in the art. Targeting can be accomplished by coupling (e.g., linking, directly or via a linker molecule, either covalently or non-covalently, so as to form a drug-antibody complex) a drug to an antibody specific for a cancer-associated polypeptide. Methods of coupling a drug to an antibody are well known in the art and need not be elaborated upon herein.

Exemplary chemotherapeutic agents include chemical compounds useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carnomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiarniprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidarnol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®, Aventis, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylomithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

Conventional compounds useful in the treatment of acute myeloid leukemia (AML) comprise, but are not limited to, topoisomerase II inhibitors, such as amsacrine, etoposide or teniposide, anitmetabolites, such as cytarabine, methotexate or mercaptopurine, or antitumor antibiotics, such as mitoxantrone, dactinomycin, daunorubicin, doxorubicin, epirubicin, homoharringtonine or idarubicin. Other conventional compounds useful in the treatment of AML considered in this invention are compounds usually applied in the treatment of ALL (acute lymphoblastic leukemia), such as asparaginase, cyclophosphamide, gemtuzumab (or any other CD 33 monoclonal antibody), ifosfamide, mesna, prednisone, topotecan, and vincristine. Under the term "conventional compound" also mixtures of the mentioned compounds are understood, e.g. combinations of cytarabine with mitoxantrone, amsacrine, daunorubicin, etoposide or idarubicin, or of cytarabine with etoposide and daunorubicin or mitoxantrone.

Any treatment regimen is applicable following the diagnosis using the markers of the invention. In one embodiment, the treatment method of the invention can include a single, a double, a triple, quadruple or more therapy comprising administering a conventional compound in combination with other conventional compounds useful in the treatment of AML.

Any therapy that is effective against acute myeloid leukemia can be used following the diagnosis of a subject using the markers of the invention. Any therapy that is effective both to treat the active disease, as well as to maintain the disease in complete or partial remission following treatment that has been effective in attaining such remission, for example bone marrow transplant or chemotherapy, is also applicable.

Following the diagnosis of the subject using the markers of the invention, different therapies for different sub-classification of acute myeloid leukemia can be used. Sub-classification of acute myeloid leukemia, as defined by either the FAB or WHO classifications, include minimally differentiated myeloid leukemia (MO), acute myeloid leukemia without maturation (M1), acute myeloid leukemia with maturation (M2), acute myeloid leukemia with maturation with t(8;21), acute promyelocytic leukemia (M3), hypergranular type acute myeloid leukemia, micro granular type acute myeloid leukemia. acute myelomonocytic leukemia (M4), acute myelomonocytic leukemia with increased marrow eosinophils (M4EO), acute Monocytic Leukemia (M5), acute monoblastic leukemia (M5a), acute monocytic leukemia with maturation (M5b), erythroleukemia, erythroid/myeloid leukemia (M6a), pure erythroid leukemia (M6b), acute megakaryoblastic leukemia (M7), acute megakaryoblastic leukemia associated with t(1;22), acute basophilic leukemia, acute myelofibrosis (acute myelodysplasia with myelofibrosis), acute leukemia and transient myeloproliferative disorder in Down's Syndrome, hypocellular acute myeloid leukemia, and myeloid sarcoma.

Kits

In one embodiment, the present invention provides a kit comprising: a means for determining methylation of at least one gene or genomic sequence selected from the group consisting of SP140, MCCC1, EHMT1, and MTSS1 and any combination thereof. In one embodiment, the kit comprises instructions for carrying out and evaluating the described method of methylation analysis.

In a further embodiment, said kit may further comprise standard reagents for performing a CpG position-specific methylation analysis.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Low Level Methylation of Tet2-DMCs Defines a Subgroup of AML That is Curable and Which Cannot be Identified Solely by Genetic and Cytogenetic Analyses Acute myeloid leukemia (AML) is curable in a subset of cases. The DNA methylation regulator TET2 is frequently mutated in AML and we hypothesized that studying TET2-specific differentially methylated regions (tet2-DMCs) improves AML classification. The results presented herein are based on the use of bisulfite-pyrosequencing to analyze the methylation status of four tet2-DMCs (SP140, MCCC1, EHMT1, and MTSS1) in a test group of 94 consecutive patients and a validation group of 92 consecutive patients treated with cytarabine-based chemotherapy. In the test cohort, hierarchical clustering analysis identified low levels of tet2-DMC methylation in 31/94 (33%) cases and these had markedly longer overall survival (median survival 72+ vs 14 months, P=0.002). Similar results were seen in the validation cohort. tet2-DMC-low status was shown to be an independent predictor of overall survival in a multiple regression analysis (Hazard ratio 0.35, p<0.0001). In the TCGA dataset where DNA methylation was analyzed by a different platform, tet2-DMC-low methylation was also associated with improved outcome (median survival 55 vs 15 months, P=0.0003) and was a better predictor of survival than mutations in TET2, IDH1, or IDH2, individually or combined. The data presented herein shows that low levels of tet2-DMC methylation defines a subgroup of AML that is highly curable and cannot be identified solely by genetic and cytogenetic analyses.

The materials and methods used in these experiments are now described.
Materials and Methods
Patients Whole bone marrow samples collected prior to treatment were analyzed from 94 AML patients for the test cohort and 92 AML patients for the validation cohort. All patients were seen and treated with chemotherapy at The University of Texas MD Anderson Cancer Center (MDACC). The Institutional Review Board at MDACC and Temple University approved these studies, and all patients gave informed consent for the collection of residual tissues as per institutional guidelines and in accordance with the Declaration of Helsinki. In this study, only patients treated with MDACC-standard cytarabine-based induction regimens were included. The patients were selected solely based on sample availability. There was no difference in survival between patients with or without available samples in the MDACC leukemia bank. The two cohorts (test and validation) consisted of consecutive patients with AML and excluded good risk cytogenetics (if known). The patients were treated on four main chemotherapy regimens (idarubicin+cytarabine, 65 patients; idarubicin+cytarabine+vorinostat, 43 patients; idarubicin+cytarabine+tipifarnib, 34 patients; idarubicin+cytarabine+sorafenib, 42 patients; fludarabine+cytarabine+GCSF+gemtuzumab, 2 patients; see FIG. 17). The four regimens gave equivalent survival in this cohort. Post remission therapy generally included 6-8 additional cycles of the same therapy at the same or reduced doses depending on toxicity. 82% and 90% of the patients achieved CR with one course in the test and validation cohorts, respectively. Standard diagnostic and remission criteria were used (Vardiman J W et al., Blood. 2002; 100(7):2292-2302).
Mutation Analysis Mutation status of FLT3 (internal tandem duplications [FLT3-ITD] and tyrosine kinase domain [FLT3-TKD]), NPM1, and RAS were obtained from clinical records and were tested in CLIA-approved clinical laboratories. We used pyrosequencing to analyze mutations of the R132 residue in IDH1, and residues R140 and R172 in IDH2 which have been reported as mutated in AML (Mardis E R, et al.; N Engl J Med. 2009; 361(11):1058-1066; and Marcucci G, et al. J Clin Oncol. 2010; 28(14):2348-2355). Mutations affecting the amino acid R882 residue in the DNMT3A gene (Ley T J, et al.; N Engl J Med. 2010; 363(25):2424-2433; and Walter M J, et al. Leukemia. 2011; 25(7):1153-1158) were analyzed by pyrosequencing. Primer sequences and PCR conditions are listed in FIG. 18.
Quantitative DNA Methylation Analyses by Bisulfite-Pyrosequencing Bisulfite-pyrosequencing was used to quantitatively assess DNA methylation 31 for 4 regions (CpG sites in SP140, MCCC1, EHMT1, and MTSS1) and >95% success rates were obtained for DNA methylation data from patients. The EpiTect Bisulfite Kit (QIAGEN) was used for bisulfite conversion of 0.5-1 μg of DNA. After bisulfite conversion, pyrosequencing was performed on the PyroMark Q96 MD platform (QIAGEN). Success rates in pyrosequencing were 100%, 100%, 98%, and 97% for SP140, MCCC1, EHMT1, and MTSS1. Primer sequences and PCR conditions are listed in FIG. 18.
Statistical Analysis Statistical analyses were performed using PRISM (GraphPad Software, Inc., CA) and the statistical computing language R (www.r-project.org). The Mann-Whitney test was used to compare continuous variables of DNA methylation levels. Fisher's exact test was used for two-by-two contingency analyses. All p values were two-tailed and the threshold of statistical significance was P<0.05. Survival data are presented using the Kaplan-Meier method and P values for different groups were generated with the logrank test, with surviving patients being censored with a median follow-up of 48 months (2 to 72 months) and 44 months (16 to 82 months) in the test and validation cohorts, respectively. The Cox proportional hazards model was used for multiple regression analysis. Multiple regression analyses were performed with covariates which were shown to be statistically significant in univariate analyses including age, antecedent hematologic disorder (AHD). European LekemiaNet (ELN) (Rollig C, et al.; J Clin Oncol. 2011; 29(20):2758-2765), IDH/DNMT3A mutation status, and tet2-DMC status were also included in multiple regression analyses. The Cox proportional hazards assumption was tested for each covariate analytically using Schoenfeld residuals. There was no evidence of nonproportional hazards. Hazard ratios (HRs) are shown with 95% CIs. Hierarchical clustering analyses were performed by ArrayTrack (http://edkb.fda.gov/webstart/arraytrack/) with the Euclidean distance dissimilarities and Ward's method.

The results of the experiments are now described.

Patients

Figure 6:
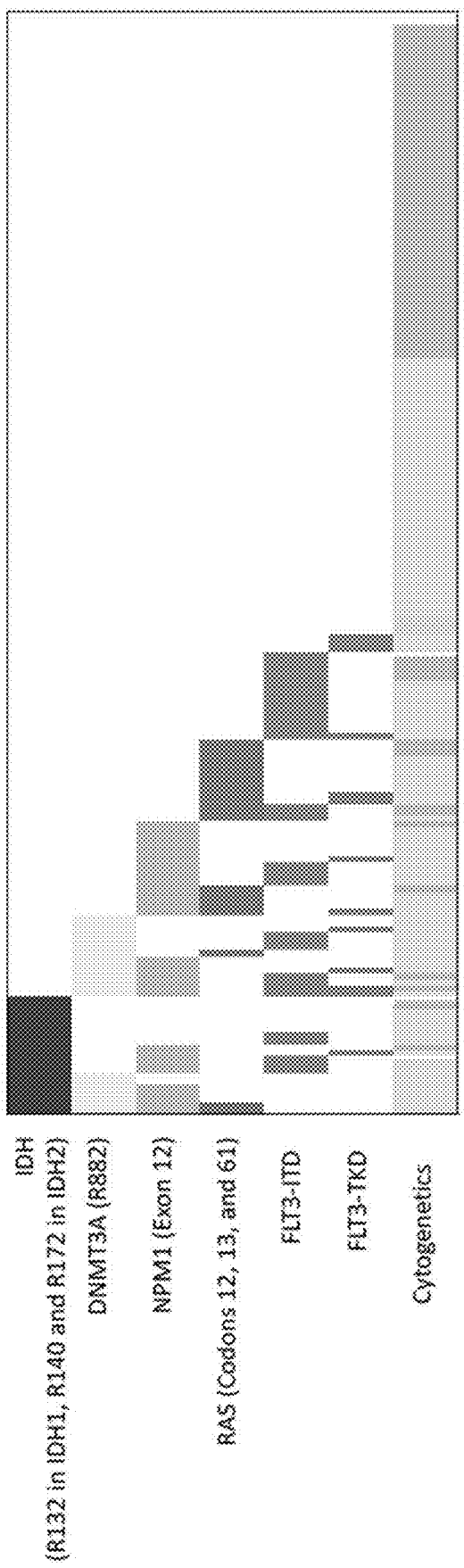
FIG. 6 depicts mutation co-occurrence for 186 AML patients. Shown are somatic, nonsynonymous mutations in individual genes and sets of genes. Eighty-one (43%) had at least one mutation in one of the listed genes or sets. The cytogenetic risk for each patient is shown at the bottom of the chart. Blue, Favorable; Green, Intermediate; Red, Poor risk groups.
Figure 7:
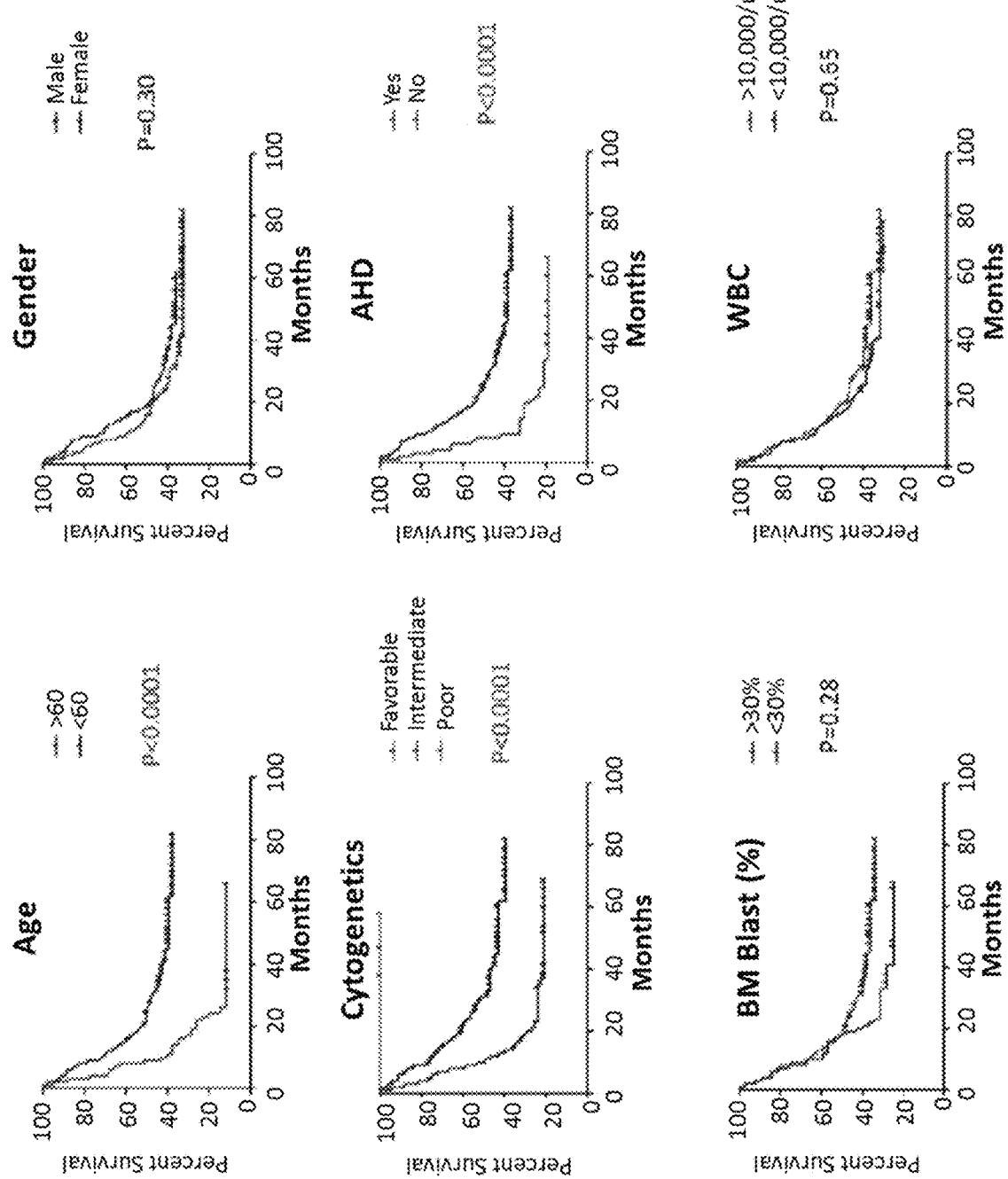
FIG. 7 depicts univariate analyses of OS by clinical characteristics for 186 AML patients. Kaplan-Meier survival curves were drawn for each covariate. Age, cytogenetics, and AHD are associated with OS. P values are derived from the log-rank test.
Figures 8A, 8B:
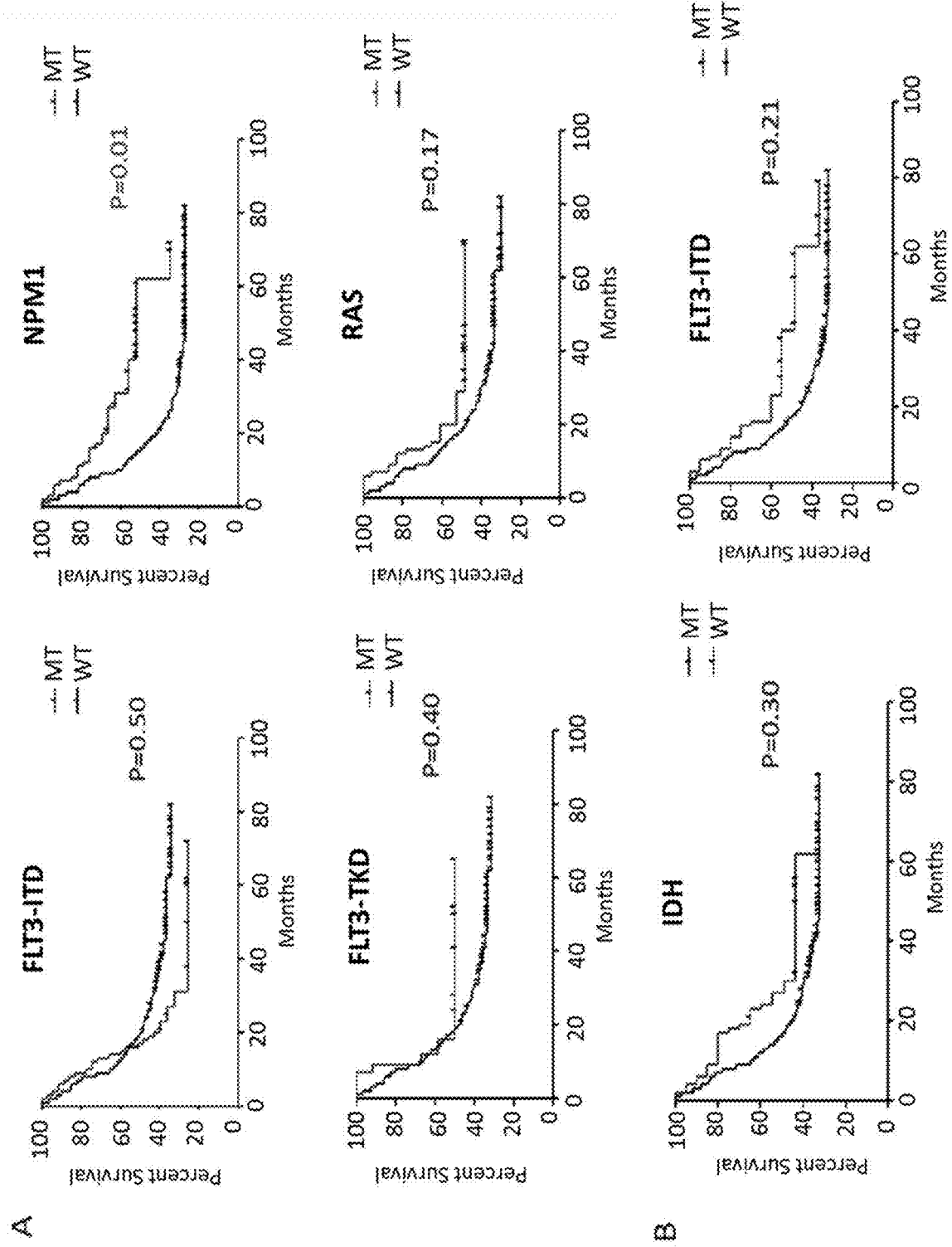
FIGS. 8A-8B, depicts univariate analyses of OS by genetic alterations for 186 AML patients. Kaplan-Meier survival curves were drawn for each gene. Only NPM1 mutations are associated with longer OS (P=0.01). P values are derived from the log-rank test.

Exerpiments were designed to study consecutive patients with adult (≥17 years of age) AML enrolled in front-line chemotherapy studies at MDACC. These clinical trials included patients up to the age of 73 and excluded favorable-risk AML when known. The clinical characteristics of the test (N=94) and validation (N=92) cohorts are shown in FIG. 1. The patients in the test and validation cohorts were accrued consecutively and were enrolled on four main clinical trials all of which had a cytarabine and Idarubicin backbone (FIG. 17). Complete remission (CR) was obtained in 73% and 78% of the patients from the test and validation cohorts, respectively, and median overall survival (OS) was 17 and 19 months in the two cohorts. Genetic alterations were identified in 81 (43%) out of 186 AML patients included in the test and validation cohort (FIG. 1 and FIG. 6). Univariate analyses revealed that age, cytogenetics, antecedent hematologic disorder (AHD) and mutations in NPM1 were associated with OS (P<0.0001 for all comparisons except for NPM1 mutations with P=0.01, FIG. 7 and FIG. 8A). Mutations in IDH1/2 and DNMT3A did not affect OS significantly (FIG. 8B).

DNA Methylation of Tet2-DMCs in AML

Figure 9A:
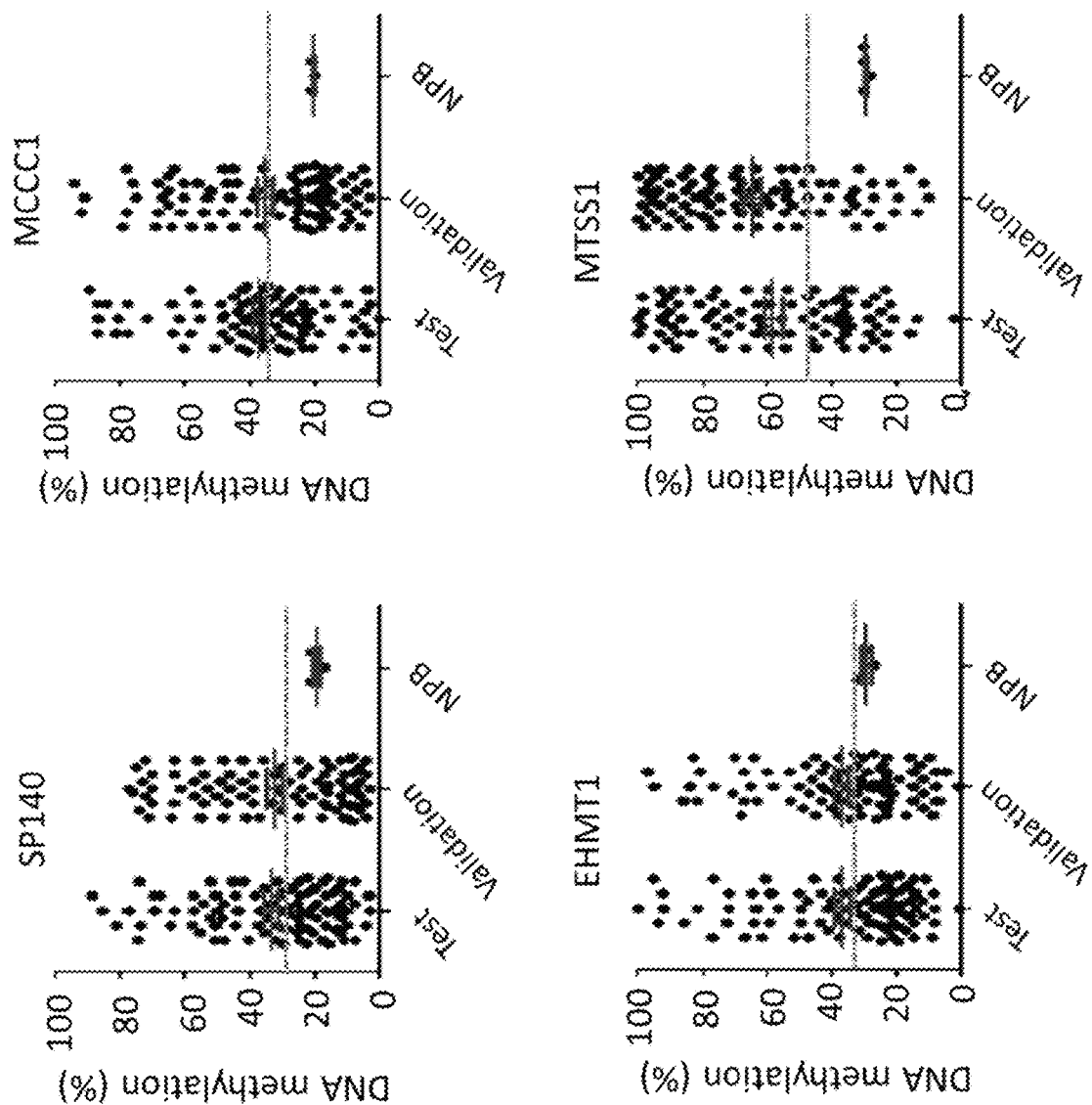
FIGS. 9A-9B, depicts DNA methylation status of 4 tet2-DMCs (a CpG site close (<50 bp) to the transcription start site of SP140 and CpG sites in gene-bodies of MCCC1, EHMT1, and MTSS1) in AML patients in the test and validation cohorts and normal peripheral blood (NPB). (A) Mean±SEM are shown. All 4 loci showed significant hypermethylation in AML compared to NPB. Note that there are some patients with tet2-DMC equal or lower than NPB. Horizontal blue lines represent the thresholds used for the clinically applicable tet2-DMC signature. (B) DNA methylation status of 4 tet2-DMCs in CD34+ and 34− cells.
Figure 9B:
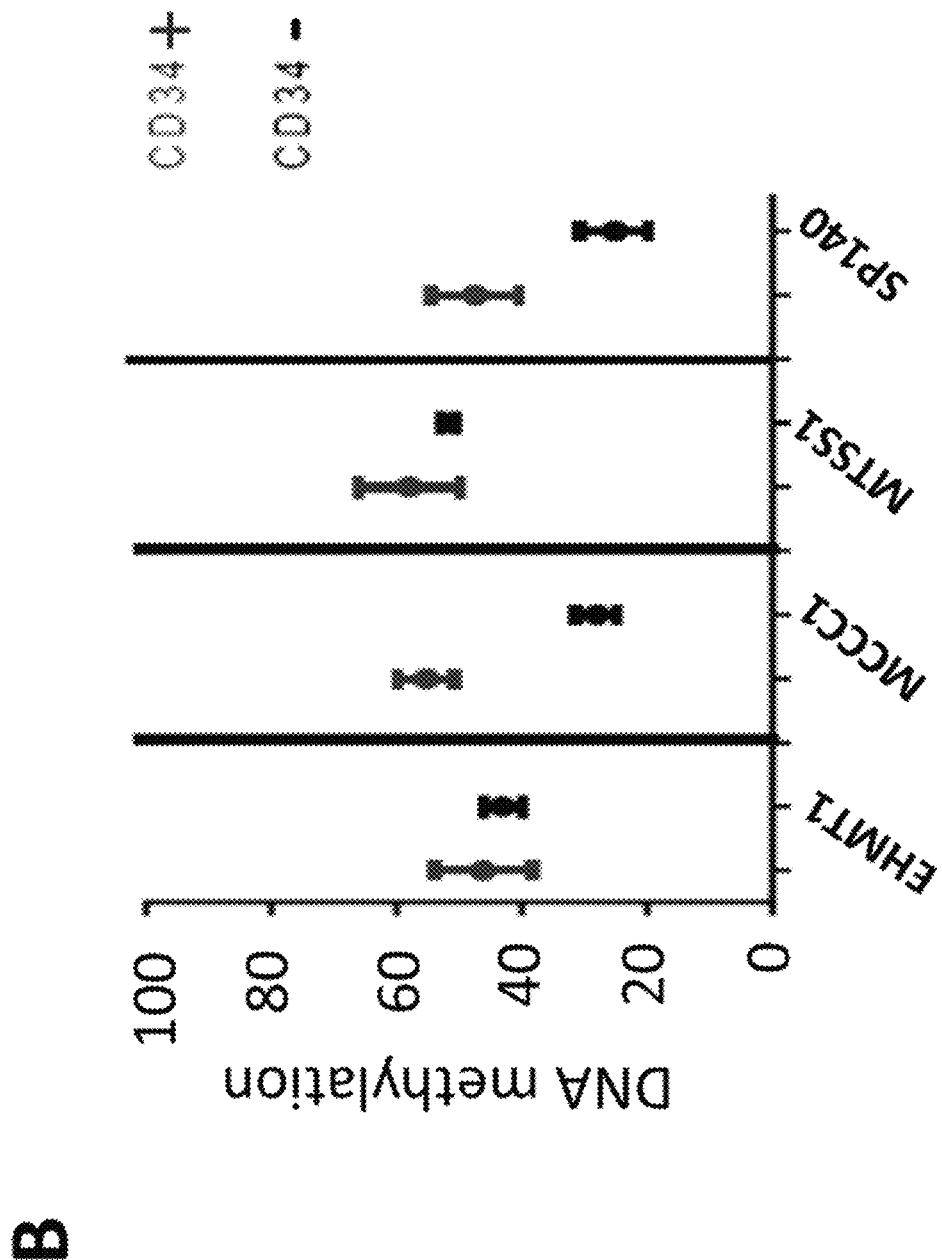

Differentially methylated CpG sites were previously identified in TET2 mutant cases of CMML (TET2-specific differentially methylated regions; tet2-DMCs) (Yamazaki J, et al.; Epigenetics. 2012; 7(2):201-207). These sites tended to be outside CpG islands and have not previously been well characterized in AML. Methylation status of 4 tet2-DMCs was measured (a CpG site close to the transcription start site of SP140 and CpG sites in gene-bodies of MCCC1, EHMT1, and MTSS1). All 4 loci showed highly variable methylation compared to normal peripheral blood (NPB) and also compared to normal bone marrow derived CD34+ or CD34− cells (FIG. 9). For each locus, a subset of cases had methylation levels equivalent to or lower than normal, while many cases were substantially higher than normal. DNA methylation of these 4 tet2-DMCs was highly concordant in AML (R=0.4-0.6, P<0.0001 for all correlations, see FIG. 19), consistent with shared DNA methylation regulation. Hierarchical clustering analysis was therefore used to define tet2-DMC methylation status. In the test cohort, a subset of 31/94 (33%) patients had low DNA methylation levels for all 4 tet2-DMCs (FIG. 3A) and clustered with NPB ("normal like tet2-DMC"). This group of patients showed significantly longer survival compared to those with higher DNA methylation (median survival 72+ vs 14 months, P=0.002, FIG. 3B). Multiple regression analysis revealed that tet2-DMC-low status along with ELN-Adverse and AHD were independent predictors of OS (P<0.0001, Hazard ratio: 0.26 for tet2-DMC-low, FIG. 20A).

Figure 21:
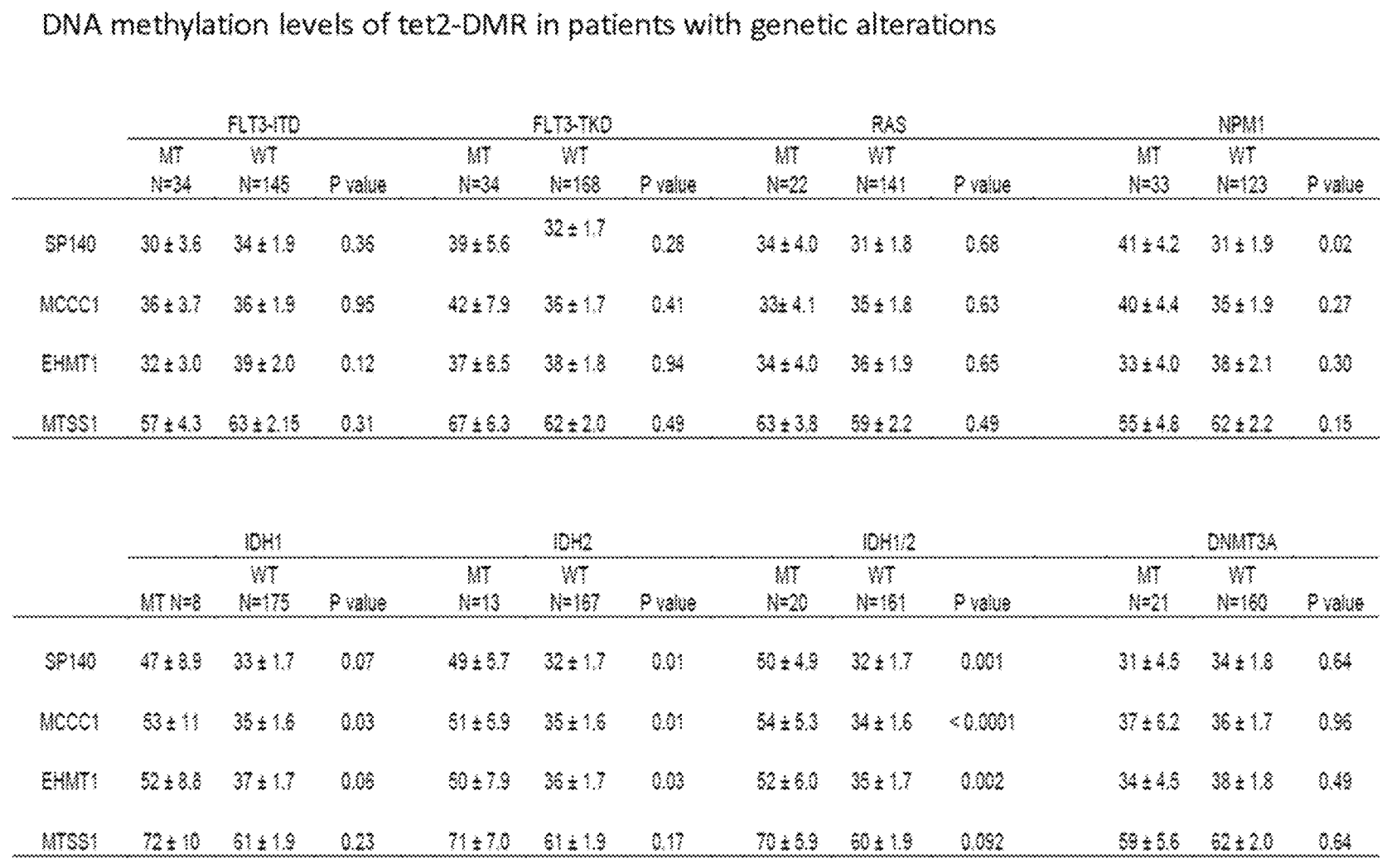

To confirm these findings, another set of 92 AML patients was investigated for validation and was found to have very similar methylation distribution at all 4 loci (FIG. 9). Once again, a subset of cases had methylation levels equivalent to or lower than normal and methylation was highly concordant. A subset of 25 patients (27%) was found to have tet2-DMC low methylation by hierarchical clustering analysis (FIG. 3C). These patients also showed significantly improved OS (median survival 74+ vs 14 months, P=0.04, FIG. 3D). Based on the remarkably consistent data between the two cohorts, they were combined to improve accuracy of the analyses. No statistical difference was found between tet2-DMC-low (N=56) and high (N=130) in the combined data (FIG. 2) in any of the clinical characteristics examined other than OS (median survival 74+ vs 14 months, P=0.0004, FIG. 4A). Effects of various mutations on DNA methylation status for the 4 tet2-DMCs was investigated and it was found that only IDH1/2 mutations were associated with significantly higher DNA methylation status (FIG. 21). Multiple regression analysis of the combined dataset revealed that tet2-DMC-low status was independently associated with a prolonged OS (P<0.0001, Hazard ratio: 0.35) along with age, unfavorable cytogenetics, ELN-Favorable classification, and AHD (FIG. 20B).

Figures 4A, 4B, 4C:
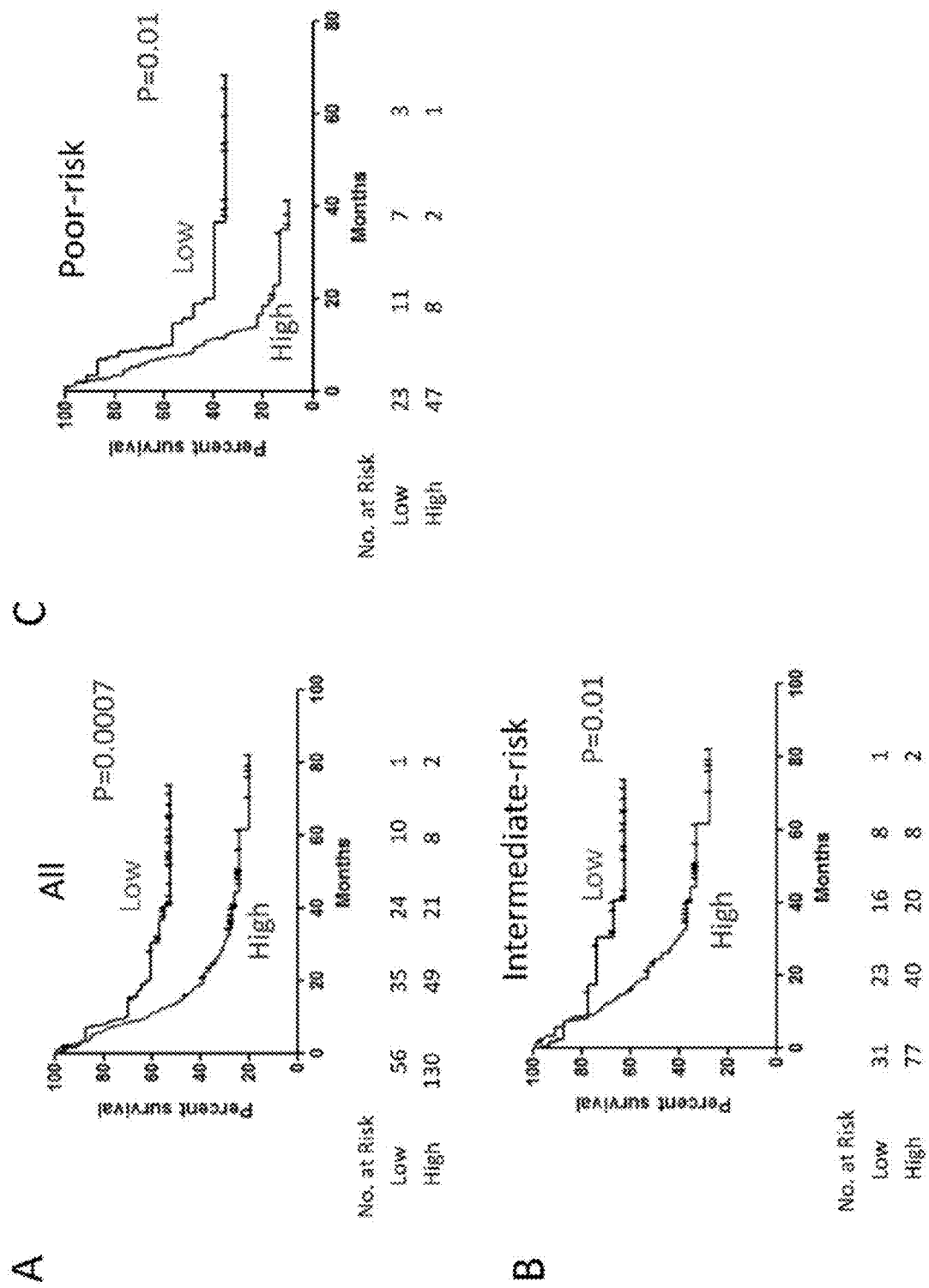
FIGS. 4A-4C, depicts Kaplan-Meier survival curves for tet2-DMC-low (blue) and -high (red) patients in the combined cohorts. Tet2-DMC-low patients showed significantly longer OS compared to tet2-DMC-high in the analysis with all patients (A), in the intermediate-risk cytogenetics group (B), and the poor-risk cytogenetics group (C). P values are derived from the log-rank test.
Figure 10:
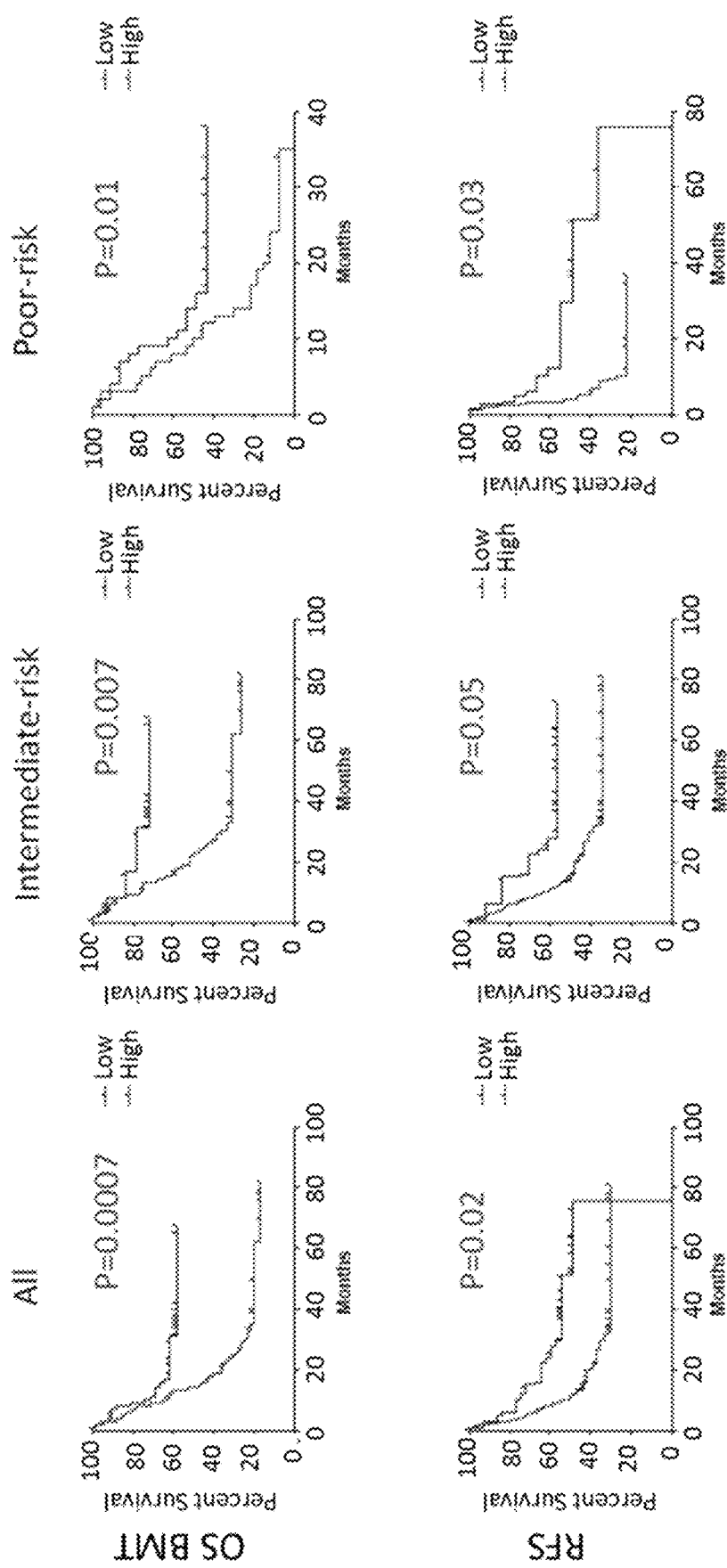
FIG. 10 depicts Kaplan-Meier survival curves for tet2-DMC-low (blue) and -high (red) patients in the combined cohorts. Curves for OS adjusted based on bone marrow transplantations (BMT) (OS BMT) and recurrence free survival (RFS) are shown in the upper and lower rows, respectively, in the analysis with all patients (left column), in the intermediate-risk cytogenetics group (center column), and the poor-risk cytogenetics group (right column), respectively. P values are derived from the log-rank test.
Figures 11A, 11B:
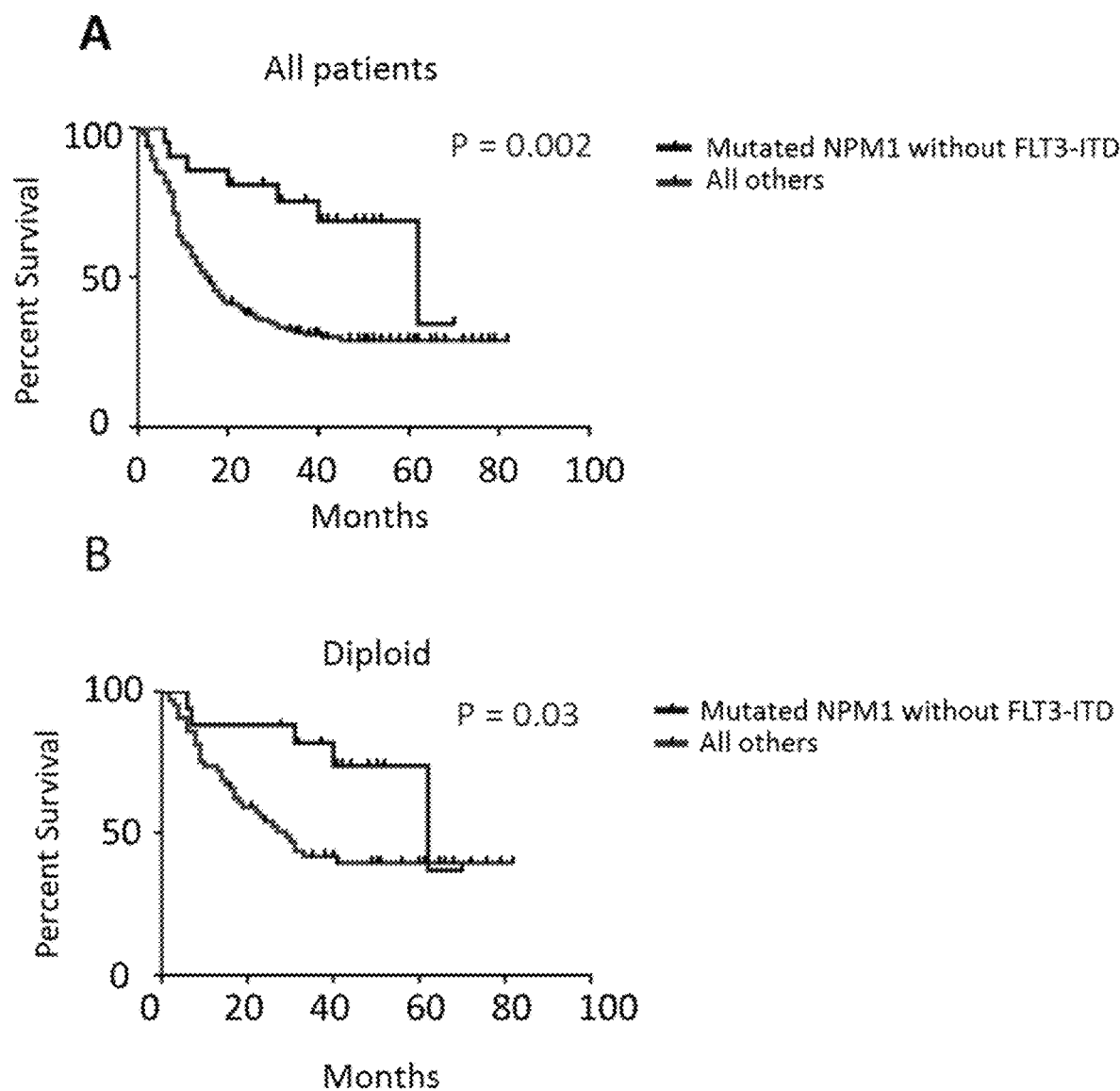
FIGS. 11A-11D, depicts Kaplan-Meier survival curves for patients with NPM1 mutation but no FLT3-ITD (N+F−) compared to other patients in the combined dataset (A) and only among diploid patients (B). Kaplan-Meier survival curves for tet2-DMC-low (blue) and -high (red) patients in (N+F−) patients (C) and all patients except for (N+F−) patients (D). P values are derived from the log-rank test.
Figure 11C:
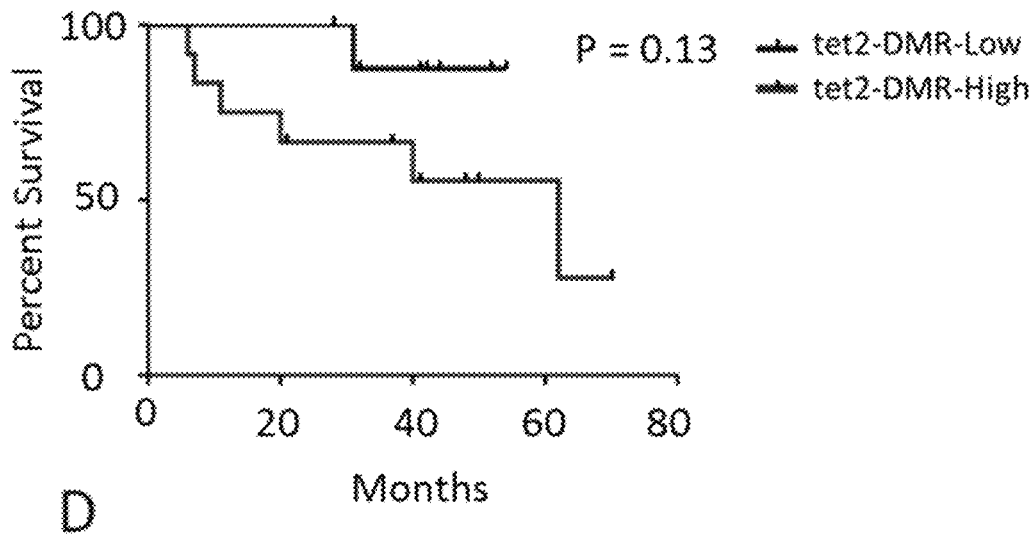
Figure 11D:
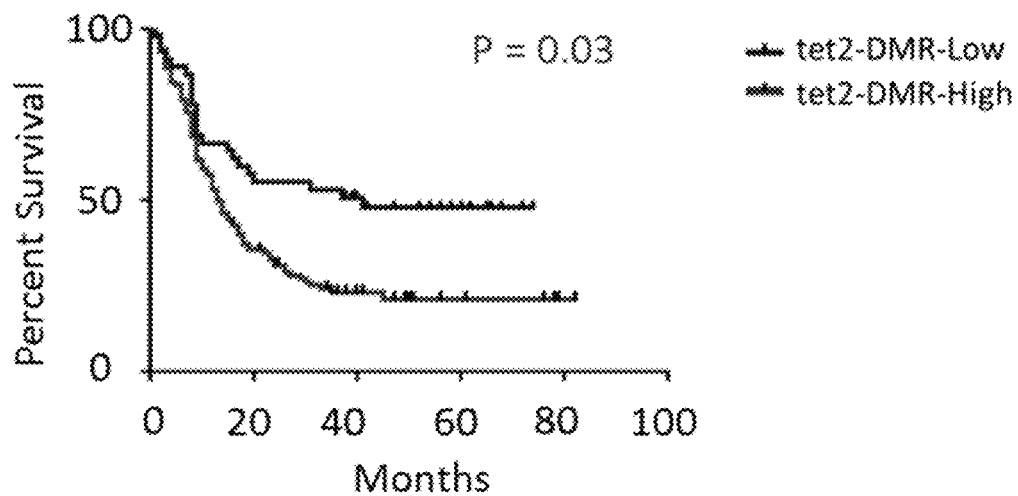

Cytogenetic status is the most consistent predictor of outcome in AML and the multiple regression analysis supported that tet2-DMC status considerably refines the classification. To illustrate this, patients with only intermediate-risk or poor-risk groups were analyzed. FIGS. 4B and 4C show that median survival was 74+ vs 23 months (P=0.01) for the Intermediate-risk group, and median survival was 16 vs 8 months (P=0.01) for the poor-risk group, in the tet2-DMC low and high groups, respectively (FIGS. 4B and 4C). FIG. 10 shows Kaplan-Meier survival curves censored at stem-cell transplantation and again tet2-DMC-low status was associated with significantly longer survival in all patients, intermediate-risk, or poor-risk groups (P=0.0007 for all cases, P=0.007 for Intermediate-risk cases, or P=0.01 for poor-risk cases, respectively). This was also the case for recurrence free survival (FIG. 10, P=0.02 for all cases, P=0.05 for intermediate-risk cases, or P=0.03 for poor-risk cases, respectively). Finally, the subset of patients with NPM1 mutation but no FLT3-ITD (N+F−) was also examind. The tet2-DMC-low group had 11 patients out of 48 (23%) with this signature, whereas the tet2-DMC-high group had 15/107 (14%) with this signature (p=0.24). N+F− patients had a better outcome (as previously reported), but this was modulated further by tet2-DMC status (FIG. 11), suggesting that they mark independent biological subsets.

A Clinically Applicable Tet2-DMC Signature

Figure 12:
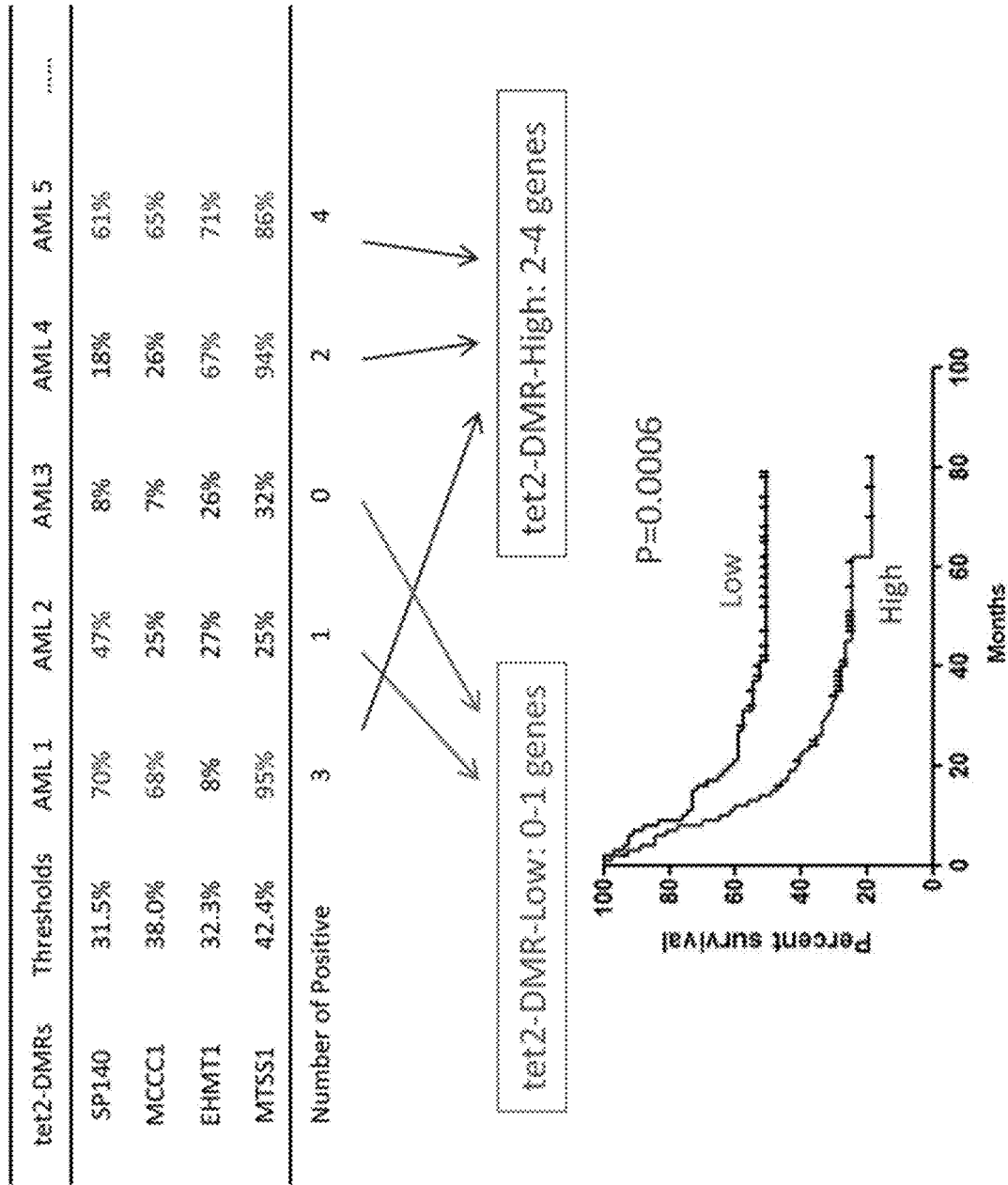
FIG. 12 depicts a scheme for a clinically applicable tet2-DMC signature. Upper panel; methylation thresholds for each tet2-DMC to classify AML patients as being called 'positive'. Examples of AML patients and the numbers of positives are shown. Lower panel; Kaplan-Meier survival curves for tet2-DMC-low (blue) and -high (red) patients defined by the method above. Tet2-DMC-low patients showed significantly longer OS compared to tet2-DMC-high in the analysis of all patients. P values are derived from the log-rank test.

A hierarchical clustering analysis requires a certain number of patients with DNA methylation status for tet2-DMCs to properly classify patients and this is not practical to guide treatment of individual patients. Therefore, a method was needed to define tet2-DMC status prospectively. To do this, thresholds were set for each tet2-DMC calculated by mean+SD for the tet2-DMC-low group. The levels of mean+SD for each tet2-DMC were 31.5%, 38.0%, 32.3%, and 42.4% for SP140, MCCC1, EHMT1, and MTSS1, respectively and methylation above these thresholds was called 'positive' for each gene (FIG. 12). AML patients were then classified into tet2-DMC-low and high based on having 0-1 or >1 genes methylated, respectively. Kaplan-Meier curves showed that patients with tet2-DMC-low (N=67) defined by this classification survived significantly longer than those who were tet2-DMC-high (median survival 79+ vs 14 months, P=0.0006). Patients with tet2-DMC-low by this classification showed higher complete remission rate (P=0.03) (FIG. 22), and multiple regression analysis showed that tet2-

DMC-low status was associated with a prolonged OS (P<0.0009, Hazard ratio: 0.49), along with ELN-Favorable, -Intermediate-1, -Intermediate-2, and AHD (FIG. 20C).

Figures 5A, 5B:
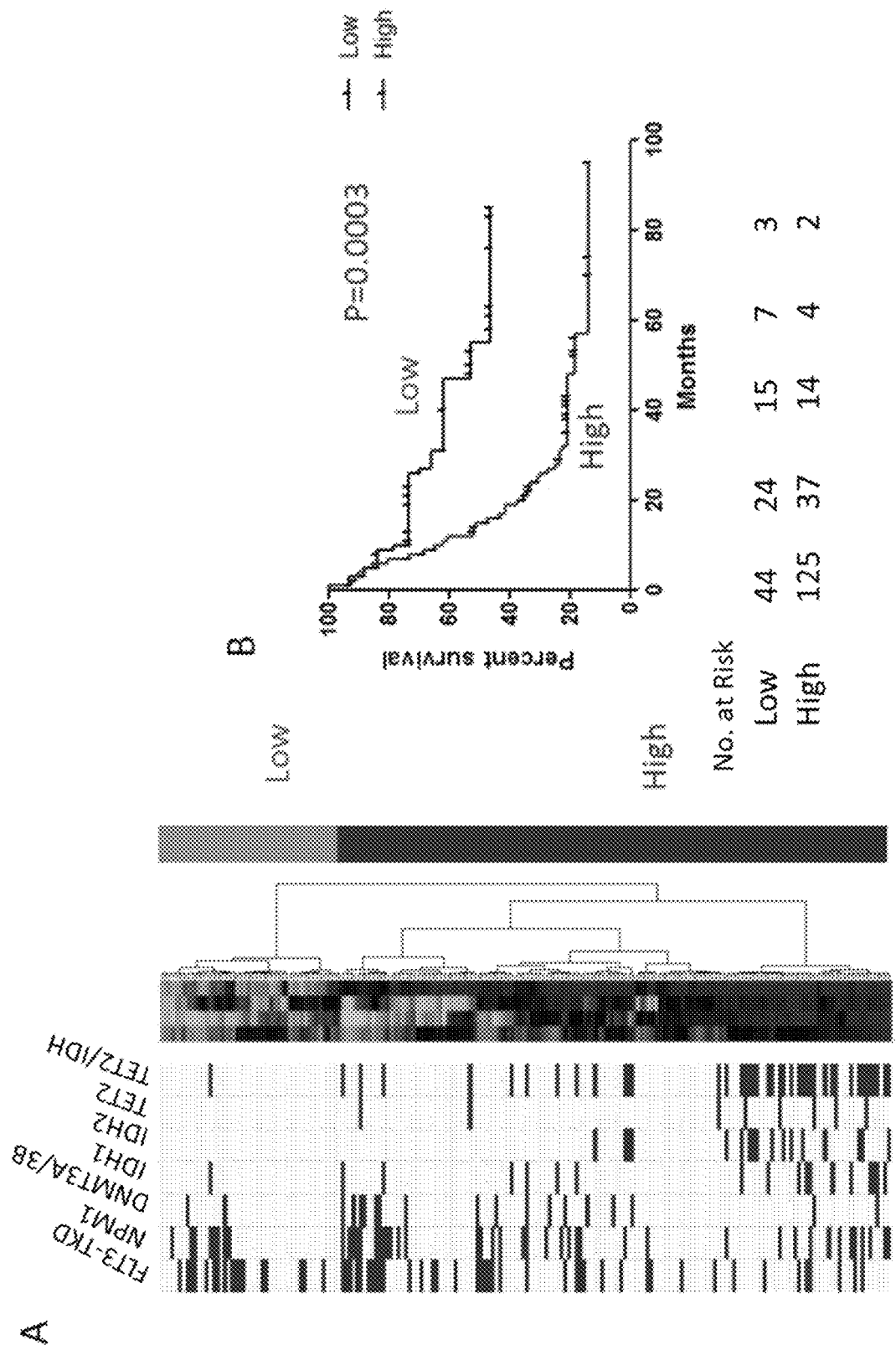
FIGS. 5A-5B, depicts DNA methylation signatures for tet2-DMC-low and -high patients in the TCGA dataset. (A) Hierarchical clustering analysis was used for classifying tet2-DMC-low and -high patients. Mutations of IDH1, IDH2 and/or TET2 are shown in red. The TET2/IDH combined column indicates mutations of either of the 3 genes. (B) Kaplan-Meier survival curves for tet2-DMC-low (blue) and -high (red) patients in the TCGA dataset. Tet2-DMC-low patients showed significantly longer OS compared to tet2-DMC-high in the analysis with all patients. P values are derived from the log-rank test.
Figure 13A:
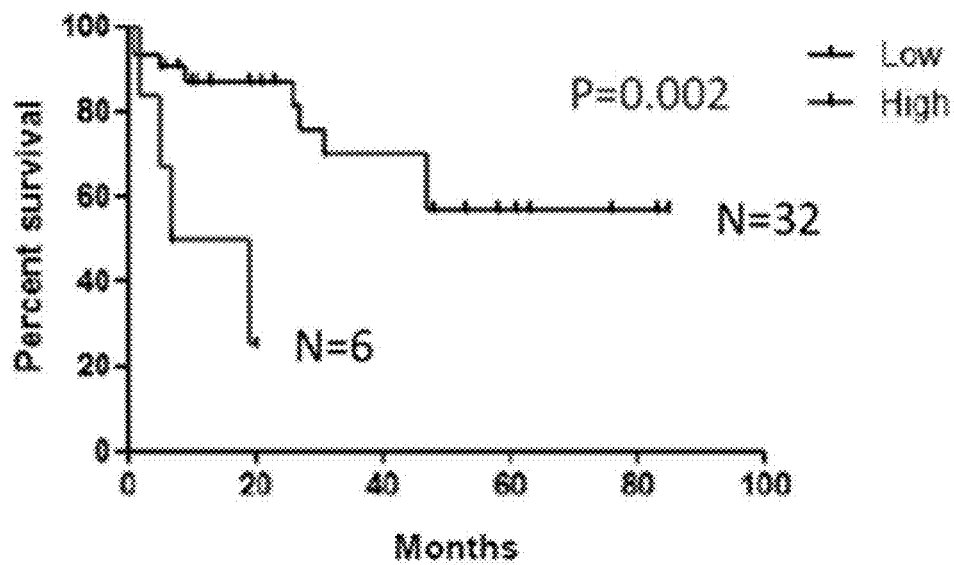
FIGS. 13A-13C, depicts additive effects between tet2-DMC-low and M3/favorable-risk cytogenetic group. (A) Kaplan-Meier survival curves in the TCGA dataset for M3/favorable-risk cytogenetic group. The patients are subdivided by tet2-DMC status. (B) Kaplan-Meier survival curves in the TCGA dataset for tet2-DMC-low patients. The patients are subdivided by status of M3/favorable-risk cytogenetic group. (C) Kaplan-Meier survival curves in the TCGA dataset for intermediate and poor cytogenetic group. The patients are subdivided by tet2-DMC status. P values are derived from the log-rank test.
Figure 13B:
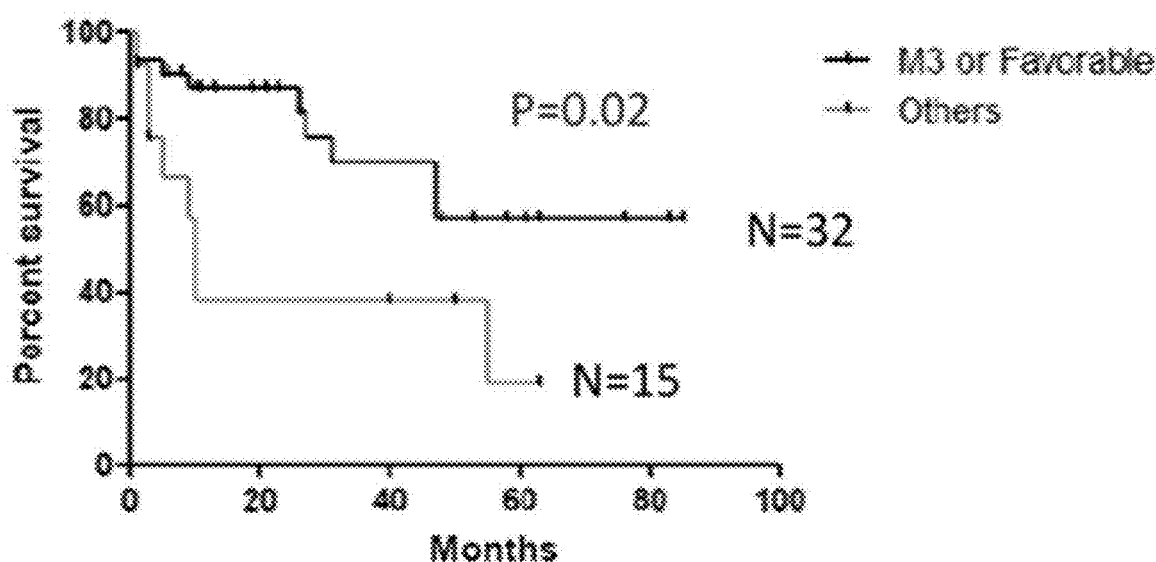
Figure 13C:
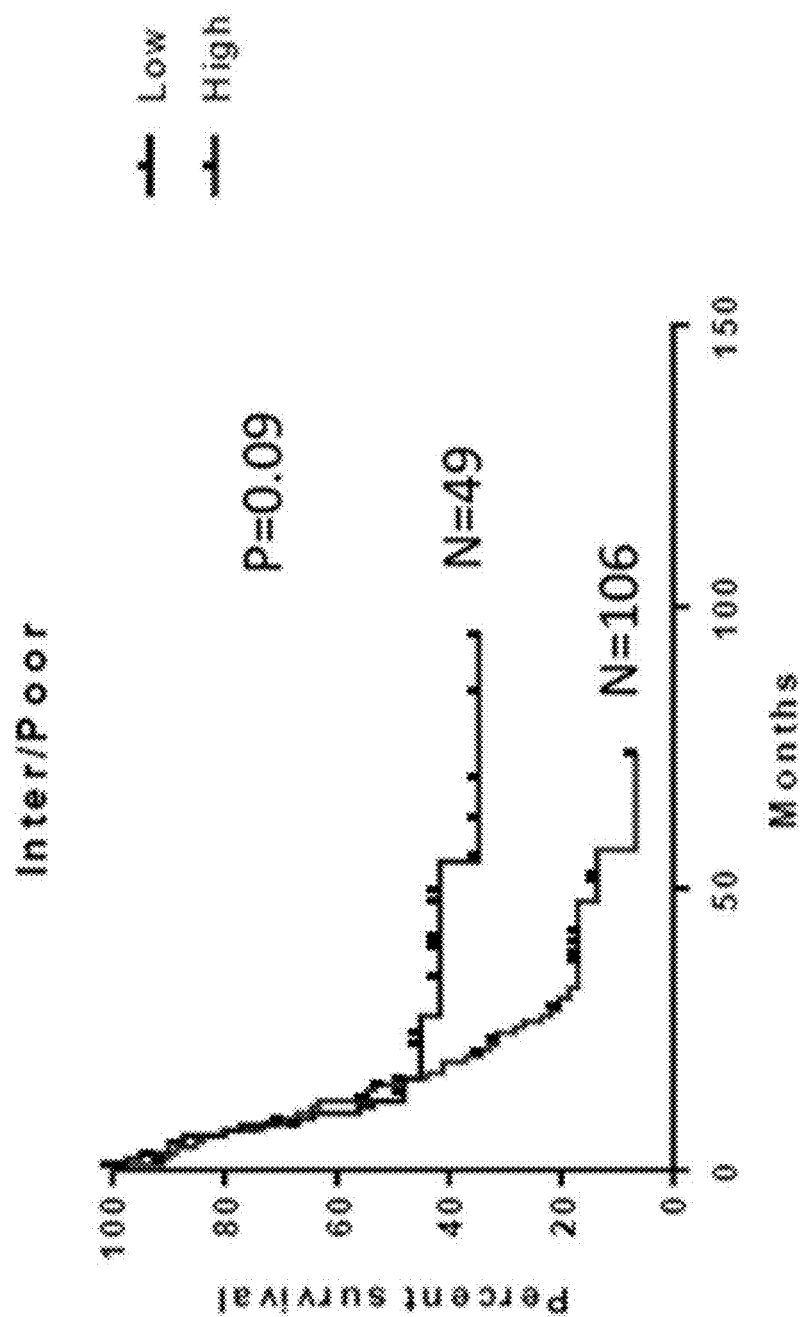

To further validate the prognostic impact of tet2-DMCs in AML, the dataset from TCGA (N Engl J Med. 2013; 368(22):2059-2074) was utilized where genome wide mutation and methylation status is available. Since the Illumina 450K Infinium platform used in TCGA analysis has probes for DNA methylation detection mostly at gene promoters, the few tet2-DMCs at promoters found in a previous study were examined. To match results from both studies, CpG probes were searched on the Infinium platform closest (<50 bp) to the sites analyzed in a restriction enzyme-based method (Jelinek J, et al.; Epigenetics. 2012; 7(12):1368-1378). Three tet2-DMCs were found at gene promoters (SP140, LSP1, and UNC93B1) whose sites analyzed by both methods nearly coincide. 1 out of the 3 non-promoter tet2-DMCs used in this study (EHMT1) was found and also added. Methylation status of these 4 tet2-DMCs was used for a hierarchical clustering analysis (FIG. 5A). In the 194 patient TCGA dataset with available outcome, tet2-DMC-low status also showed significantly longer OS (FIG. 5B, median survival 55 vs 15 months, P=0.0003). Interestingly, these tet2-DMC-low patients were younger (P<0.001), and had more often the M3 subtype and/or favorable-risk cytogenetics compared to the other groups (P<0.0001 and P<0.0001, respectively) (FIG. 23). When only patients with M3 or favorable-risk cytogenetics were analyzed, the tet2-DMC-low subgroup showed significantly longer survival than the tet2-DMC-high subgroup (P=0.0018) (FIG. 13A). On the other hand, M3 or favorable-risk cytogenetics patients were also found to have longer survival than the rest of the patients when only tet2-DMC-low patients were analyzed (P=0.023) (FIG. 13B), suggesting that tet2-DMC-low status has additive beneficial effects on survival in AML along with known favorable-risk status such as cytogenetics and M3. Finally, when APL and good risk AMLs were excluded from the TCGA dataset, tet2-DMC methylation status showed exactly the same trend as the MDACC patients with a large difference in survival favoring the tet2-DMC-low group, though the survival difference did not reach significance (p=0.09) (FIG. 13C).

Figure 14:
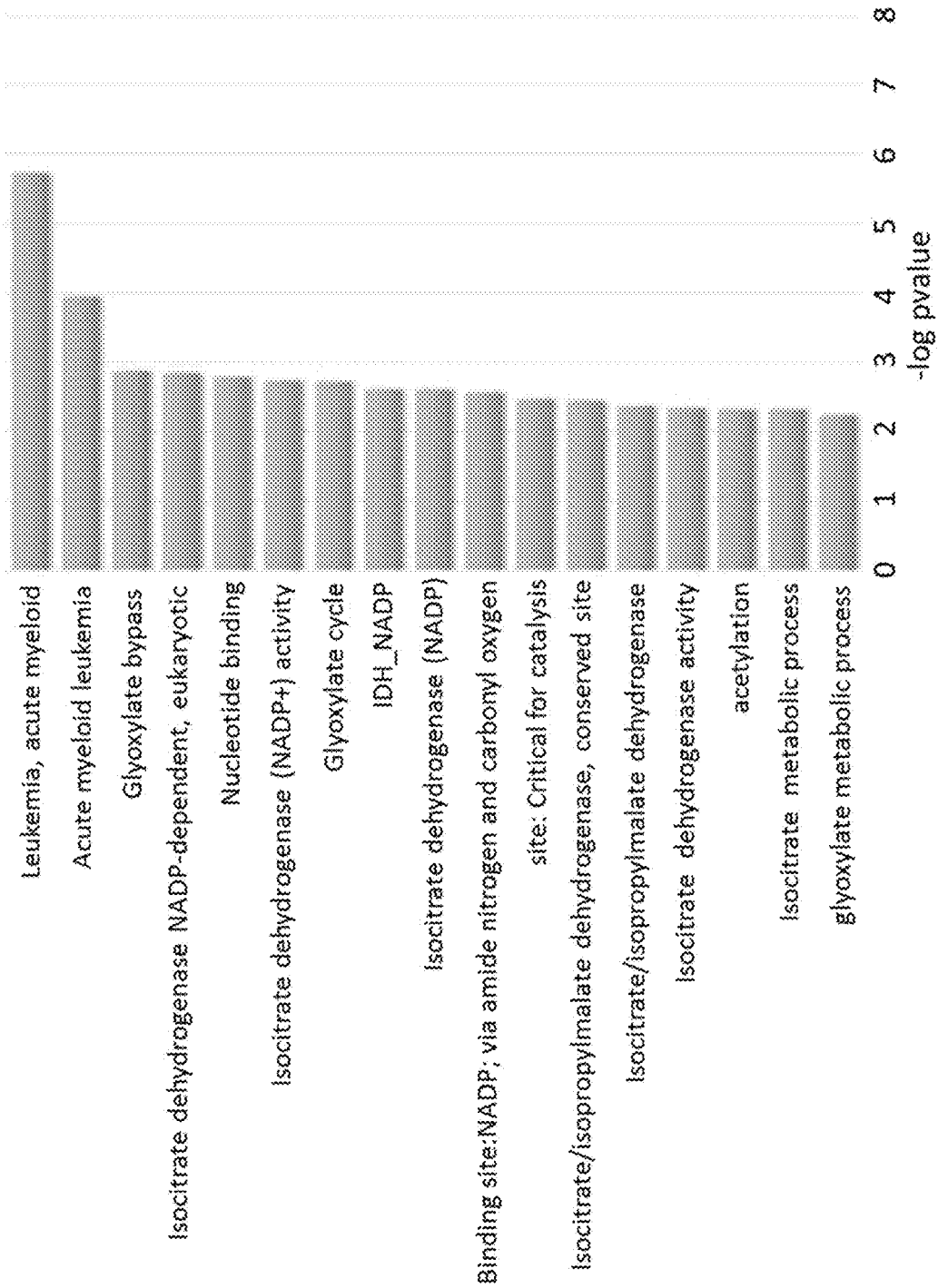
FIG. 14 depicts gene ontogeny analysis for genes mutated in patients of tet2-DMC-high with TET2/IDH mutation (upper), tet2-DMC-high without TET2/IDH mutation (middle), and tet2-DMC-low. Only categories found to be significant (p<0.05) are shown.
Figure 14:
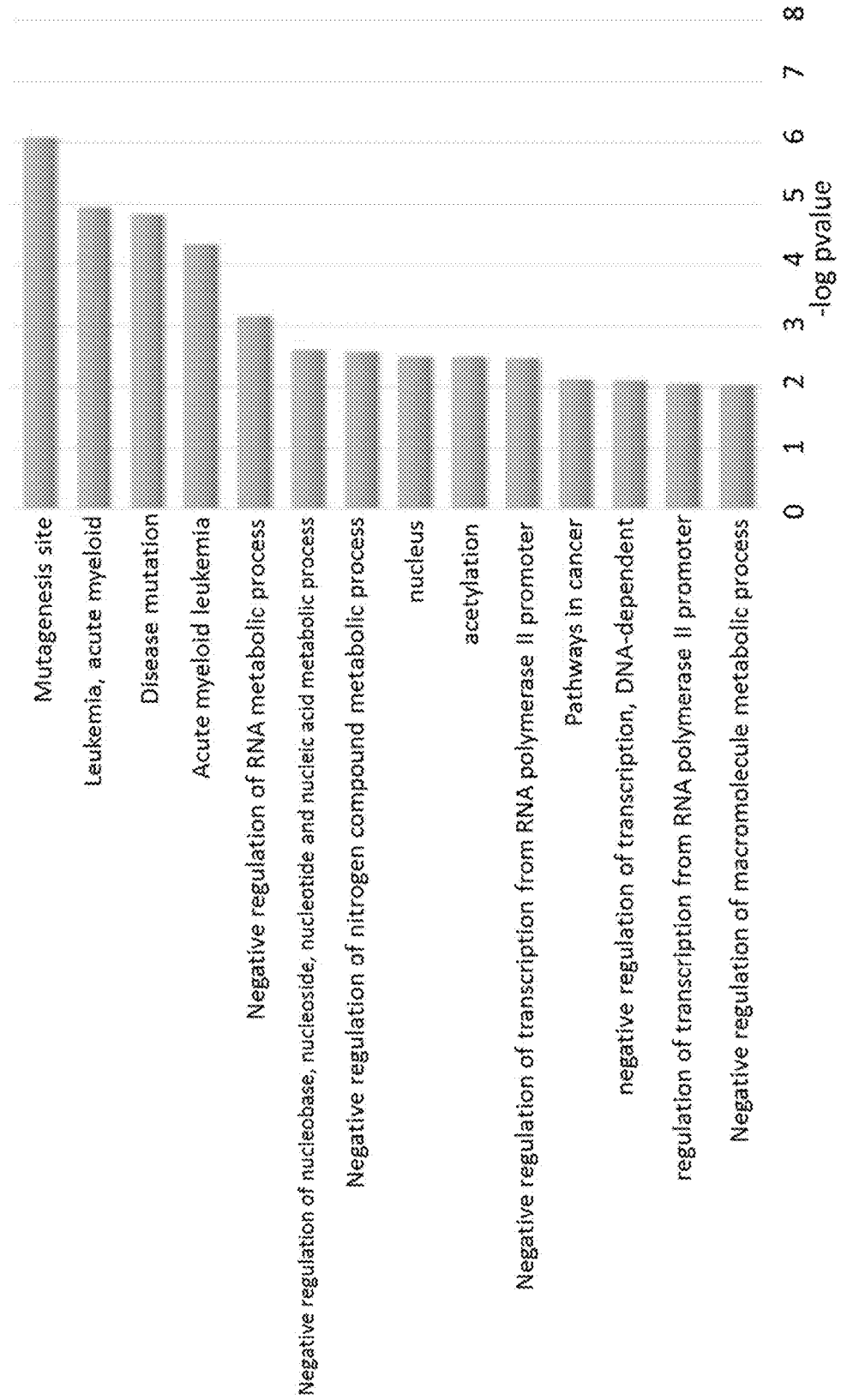
Figure 14:
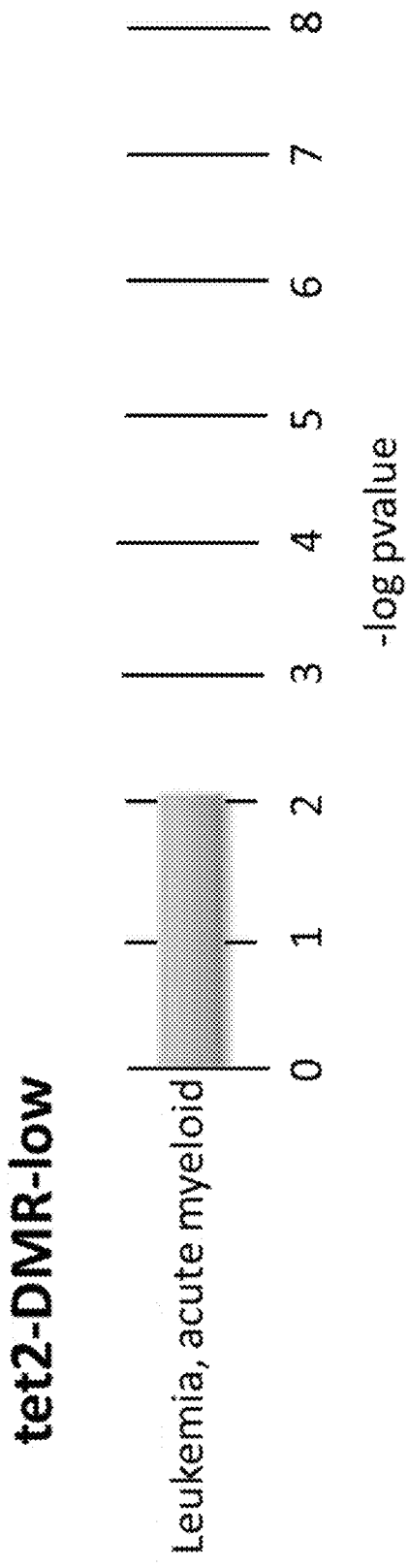
Figure 15:
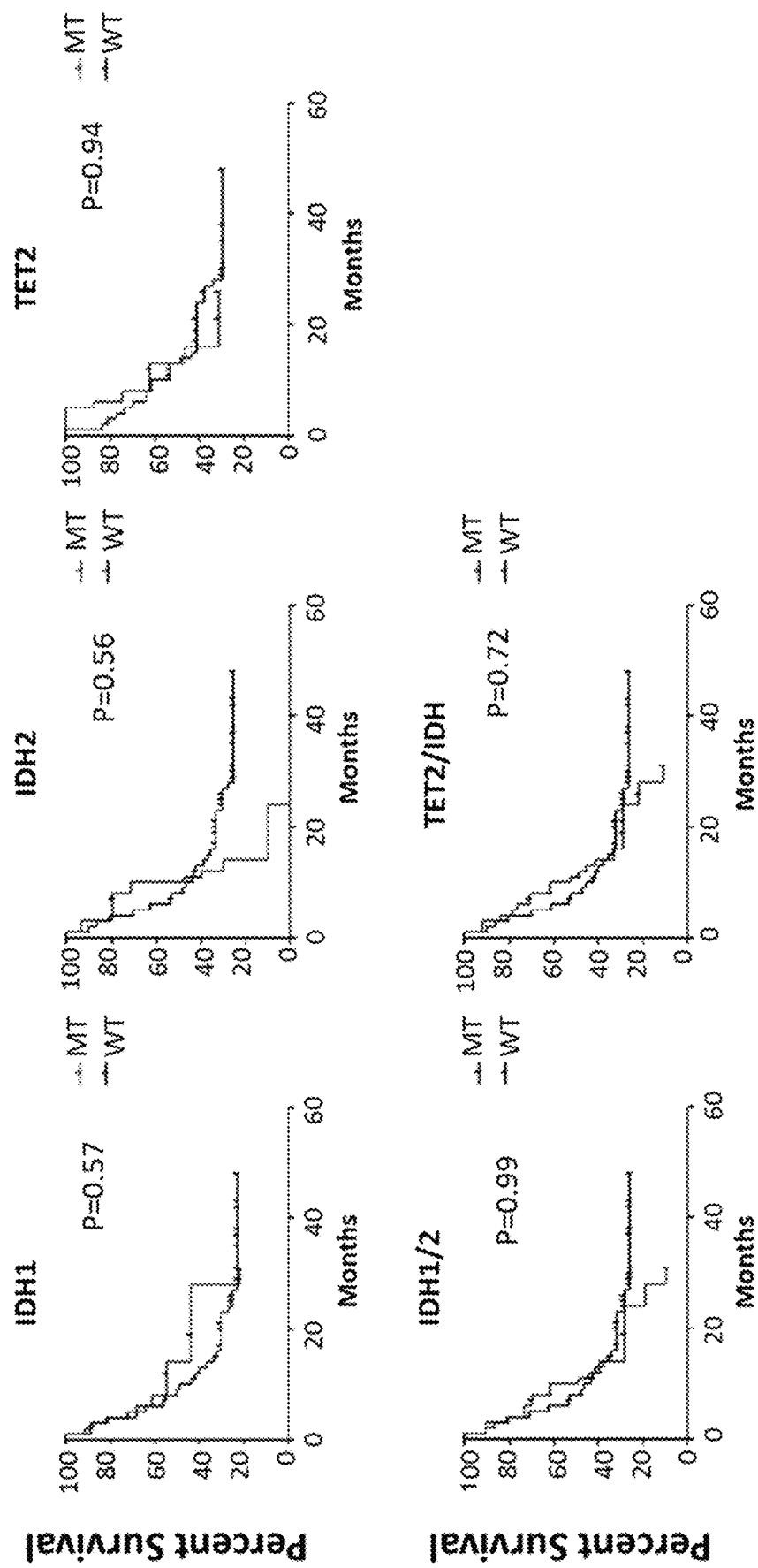
FIG. 15 depicts univariate analyses for OS of patients with mutations of IDH1, IDH2, or TET2 individually or in combination in the TCGA dataset. Kaplan-Meier survival curves were drawn for each gene. Note that none of them have an effect on the survival. P values are derived from the log-rank test.
Figure 16:
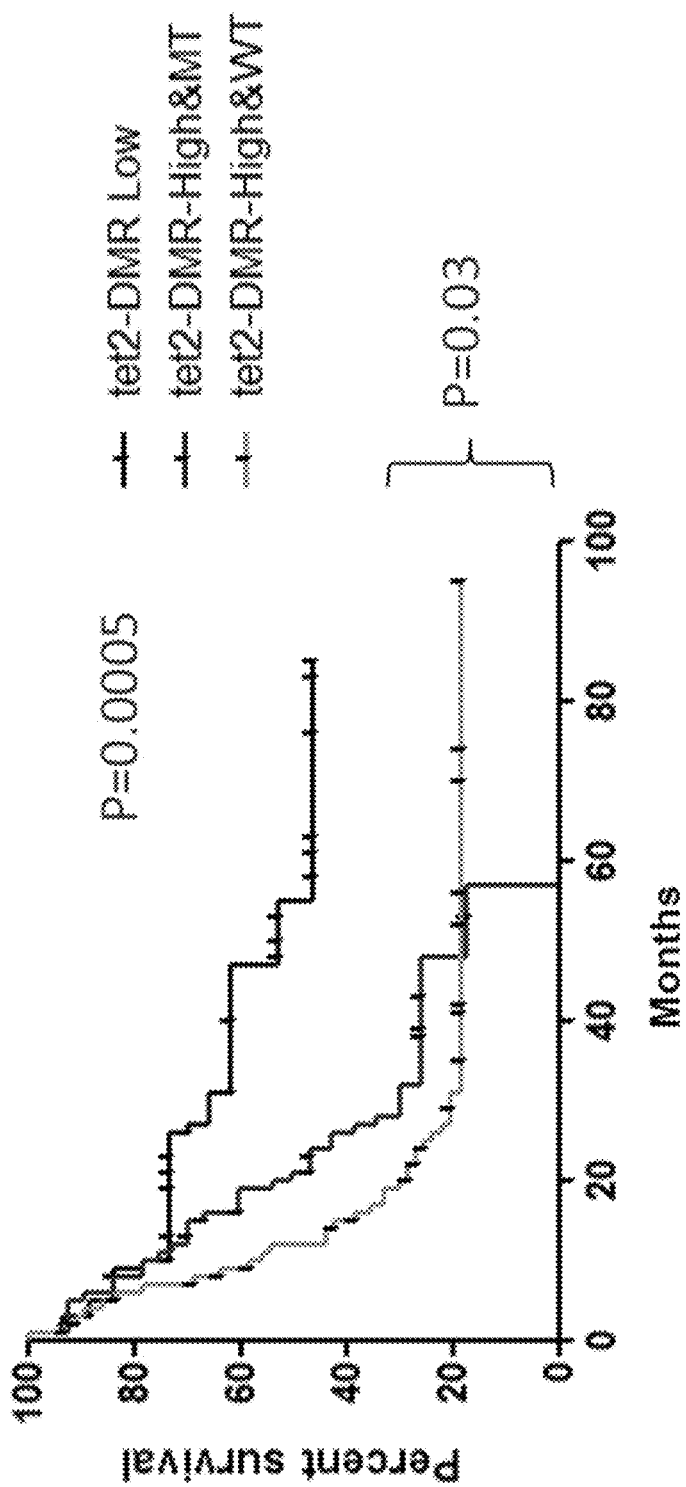
FIG. 16 depicts Kaplan-Meier survival curves for OS of patients based on their tet2-DMC and TET2/IDH mutation status. The tet2-DMC-low status (blue) shows mutations (red) and the tet2-DMC-high without TET2/IDH mutations (orange).

As expected, IDH2 mutations were significantly higher in the tet2-DMC-high groups and TET2 and IDH1 mutations were exclusive to the tet2-DMC-high group. No clinical or genetic characteristic studied was found to be significantly different between tet2-DMC-high with or without TET2/IDH mutation (FIG. 24). The complement of genes mutated in each of the subsets was also examined by gene ontology analysis and relatively minor differences were found (FIG. 14). Mutations of IDH1, IDH2, or TET2 had no effect on survival individually or in combination in the TCGA dataset (FIG. 15), in contrast to the tet2-DMC-low status which was highly significant. When combining mutation and methylation data, it was found that tet2-DMC-low status (all but one patients had no mutation of TET2/IDH) is predictive of the longest survival (median survival, 55 months; P=0.0005) followed by tet2-DMC-high with TET2/IDH mutations (median survival, 21 months), and tet2-DMC-high without TET2/IDH mutations (median survival, 12 months) (P=0.03 for tet2-DMC-high with and without TET2/IDH) (FIG. 16). Thus, tet2-DMC methylation was a better predictor of outcome than mutations in the TET2/IDH axis, but a combined methylation/mutation analysis was best for delineation of prognostically distinct subgroups.

DNA Methylation Signature at Tet2-DMCs Defines Clinically Distinct Groups of Adult AML Cases Personalized medicine requires detailed molecular classification of patients to provide a specific therapy for an individual's condition. Cytogenetics and genetics have been used for decades in this regard in AML. Cytogenetic classification is useful for predicting prognosis and assigning specific therapies in AML. Mutations in genes such as NPM1 and DNMT3A were previously found to be prognostic as well (Ley T J, et al.; N Engl J Med. 2010; 363(25): 2424-2433; and Becker H, et al. J Clin Oncol. 2010; 28(4):596-604). DNA methylation is frequently abnormal in AML and DNA methylation patterns can be prognostic (Figueroa M E, et al.; Cancer Cell. 2010; 17(1):13-27; Bullinger L et. al.; Blood. 2010; 115(3):636-642; Deneberg S., et al; Leukemia. 2010; 24(5):932-941), though the underlying mechanism(s) remains to be fully understood. Recently, epigenetic regulators such as TET216 and IDH1/229 have been found to be mutated in AML; however, their effects on prognosis is controversial, and it remains unclear if these could have a significant impact on improving the current classification systems. Since TET2/IDH potentially affect the same molecular pathways to regulate DNA demethylation (Figueroa M E, et al.; Cancer Cell. 2010; 18(6): 553-567), we hypothesized that DNA methylation status could integrate upstream defects and provide better markers for prognosis and therapy.

In this study, it was found that a DNA methylation signature at tet2-DMCs defines clinically distinct groups of adult AML cases. Patients with normal-like tet2-DMC methylation status have significantly longer OS, independently of currently used prognostic factors such as age or cytogenetics. Cure rate in tet2-DMC-low patients treated with chemotherapy exceeded 50%, as compared to less than 20% in tet2-DMC-high patients. Remarkably, this difference could also be seen in AML with poor-risk cytogenetics, where cure rates were almost 40% in tet2-DMC low patients compared to 10% in tet2-DMC-high patients. The cure rate in patients with intermediate-risk cytogenetics and tet2-DMC-low (about 60%) is nearly as good as that seen in patients with favorable-risk cytogenetics. The underlying mechanism of this difference in survival warrants further investigation. Without wishing to be bound by any particular theory, it is believed that AML cases with low tet2-DMC methylation have a preserved capacity for differentiation which may explain chemosensitivity. Experiments were designed to develope a clinically applicable tet2-DMC signature with similar findings. There was a small difference in the number of patients labeled tet2-DMC-low by cluster analysis (N=56) vs. the clinical signature (N=67) suggesting that there is room for further improvements in the prognostic signature.

Prognostic classification impacts treatment in AML. Patients with favorable-risk cytogenetics respond to chemotherapy dose-intensification; patients with poor-risk cytogenetics are routinely referred for stem-cell transplantation, while management of patients with diploid cytogenetics is variable. The data suggest testing a prospective new stratification for treatment strategies; chemo-intensification for patients with tet2-DMC-low who are likely to response well to conventional chemotherapies and new treatments or an early decision for stem-cell transplantation for patients with tet2-DMC high. It would be of interest to find out if DNA methylation inhibitors, now routinely used in treatment of elderly AML, could improve the chemosensitivity of tet2-DMC-high AML cells by hypomethylation of these tet2-DMCs to restore differentiation potential.

It is worth noting that methylation status of tet2-DMC is a better indicator of outcome than TET2 mutations or a combined TET2/IDH mutation index. This is due to the fact that mutations of TET2/IDH1/2 are identified only in a subset of AML patients with tet2-DMC-high status. It is possible that dysregulated DNA methylation at tet2-DMCs is associated with AML even in the absence of these mutations. More broadly, the data show that classification schemes that incorporate epigenetic and genetic information may be more efficient for personalized medicine. Despite the fact that different sets of tet2-DMCs were used in initial cohorts than in the TCGA dataset (due to technical differences between the methylation platforms used), similar trends were found regarding a prognostic impact of tet2-DMCs on survival. Although four markers were used in this study, it is believed that adding other tet2-DMCs to the panel improves its ability to predict survival in AML.

Recently, Marcucci et al (Marcucci G, et al.; J Clin Oncol. 2014; 32(6):548-556) reported a novel seven gene biomarker set with promoter DMCs whose DNA methylation and gene expression were associated with outcome in AML. Six out of these seven genes were detectable with DREAM, the deep sequencing-based technique used here to identify tet2-DMCs in a CMML cohort (Submitted and currently revised). None of them showed differential levels of DNA methylation in TET2 mutated cases (the promoters were mostly unmethylated at <2% in both MT and WT), which is consistent with the present finding that most tet2-DMCs are located at non-CpG island and non-promoter sites. Broadly, it would be important to integrate models of outcome in AML that incorporate both tet2-DMCs and other differentially methylated sites.

The interactions between the tet2-DMC-low signature with known prognostic markers in AML is an interesting question to pursue. No significant enrichment of NPM1 mutant patients were found in the tet2-DMC low subgroup though the patient numbers remain small. The CCAAT/enhancer binding protein a (CEBPA) has gained increasing attention as a favorable prognostic factor in acute myeloid leukemia (AML) (Preudhomme C, et al. Blood. 2002; 100 (8):2717-2723; and Green C L, et al.; J Clin Oncol. 2010; 28(16):2739-2747). In the TCGA dataset where CEBPA mutation status is available, there were no tet2-DMC-low patients with CEBPA mutations, implying that the tet2-DMC signature is CEBPA independent.

In summary, the results presented herein demonstrate that low level methylation of tet2-DMCs defines a subgroup of AML that is curable and which cannot be identified solely by genetic and cytogenetic analyses. This finding may lead to new clinically useful biomarkers for prognosis in AML and to a better risk-stratification for treatment.

Example 2: DNA Methylation Status of SP140, MCCC1, EHMT1, and MTSS1

DNA methylation of several genes in AML was measured by bisulfite-pyrosequencing, which is one of the most reliable ways to analyze DNA methylation for individual genes. About 200 patients with AML were studied; patients were divided into groups according to their DNA methylation level in each gene. The groups were compared for treatment outcome and survival after chemotherapy. The methylation-based classifiers were compared to known prognostic factors in AML such as age and type of cytogenetics.

Four genes that strongly predicted survival in AML were found (SP140, MCCC1, EHMT1, and MTSS1). SP140 is a component of the nuclear body, which is believed to have function in the pathogenesis of acute promyelocytic leukemia and viral infection. MCCC1 encodes the large subunit of 3-methylcrotonyl-CoA carboxylase. This enzyme functions as a heterodimer and catalyzes the carboxylation of 3-methylcrotonyl-CoA to form 3-methylglutaconyl-CoA. EHMT1 encodes a histone methyltransferase that is part of the E2F6 complex, which represses transcription. The encoded protein methylates the Lys-9 position of histone H3, which tags it for transcriptional repression. This protein is believed to be involved in the silencing of MYC- and E2F-responsive genes and therefore could play a role in the G0/G1 cell cycle transition. MTSS1 is believed to be related to cancer progression or tumor metastasis in a variety of organ sites through an interaction with the actin cytoskeleton.

Figure 25:
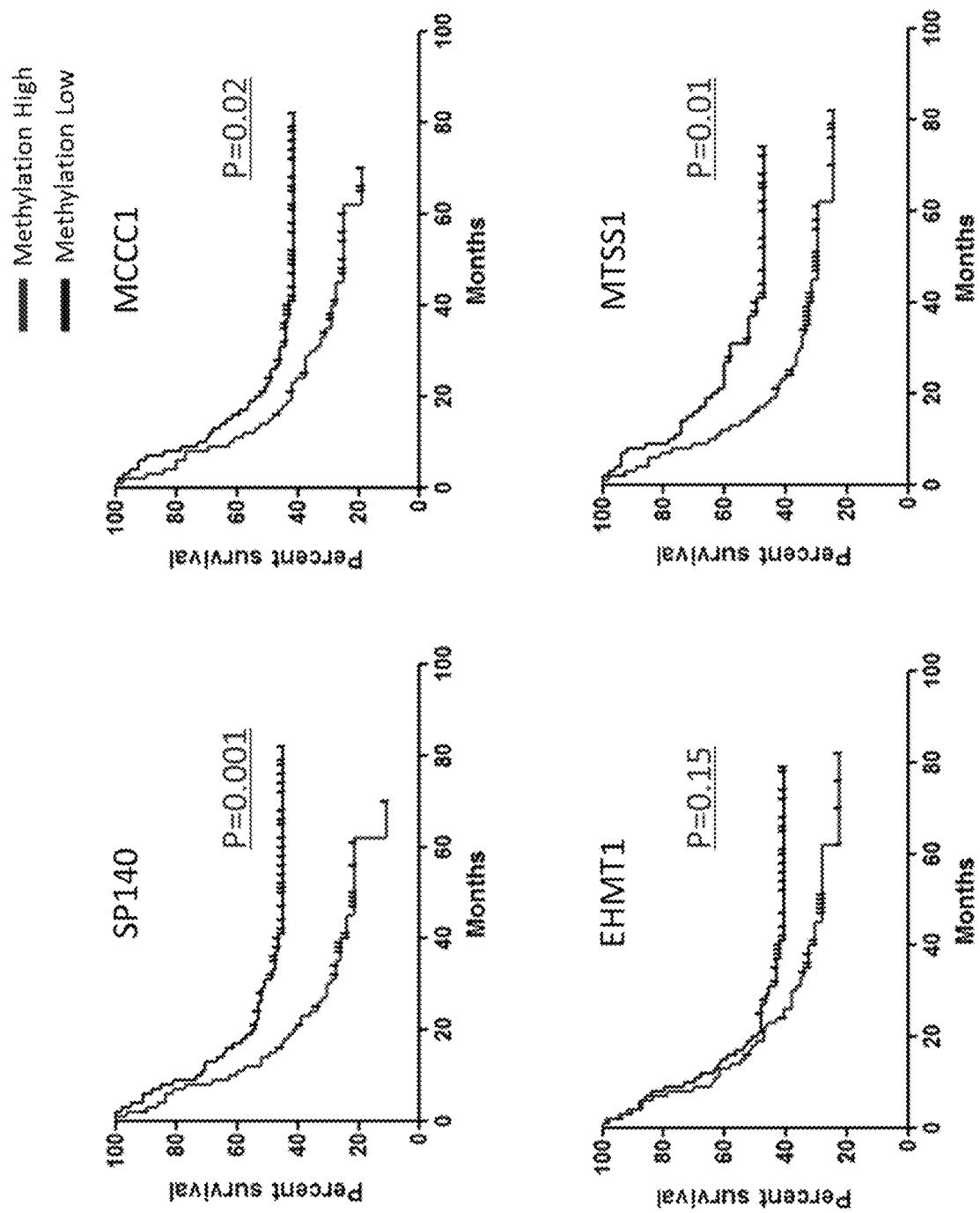
FIG. 25 is an image demonstrating that patients with DNA methylation levels below the level of the threshold for each of SP140, MCCC1, EHMT1, and MTSS1, showed longer survival compared to patients with high DNA methylation.
Figure 26:
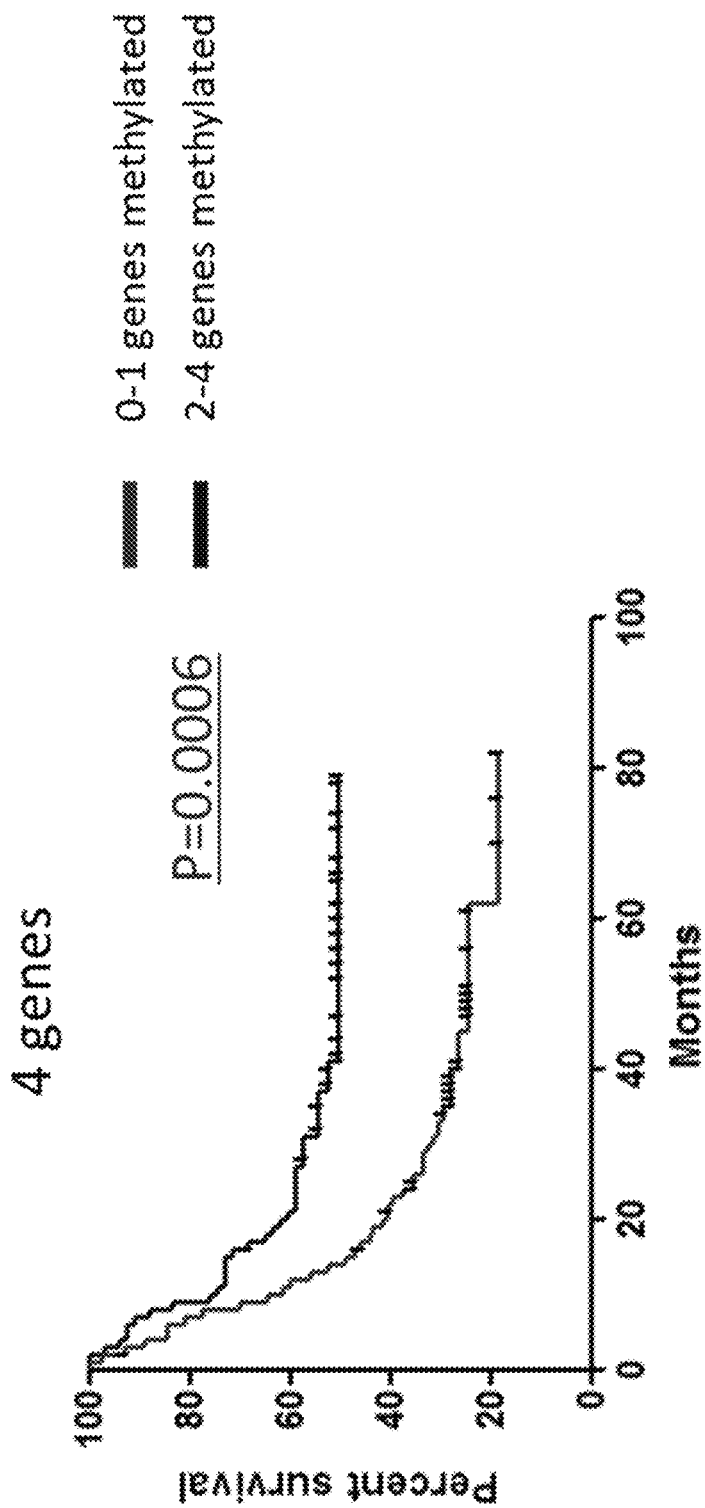
FIG. 26 is an image demonstrating that the count of methylated genes above thresholds for each of SP140, MCCC1, EHMT1, and MTSS1 (count of 0-1 or >1 methylated among the four genes) had even greater significance than single gene measurements.
Figure 27:
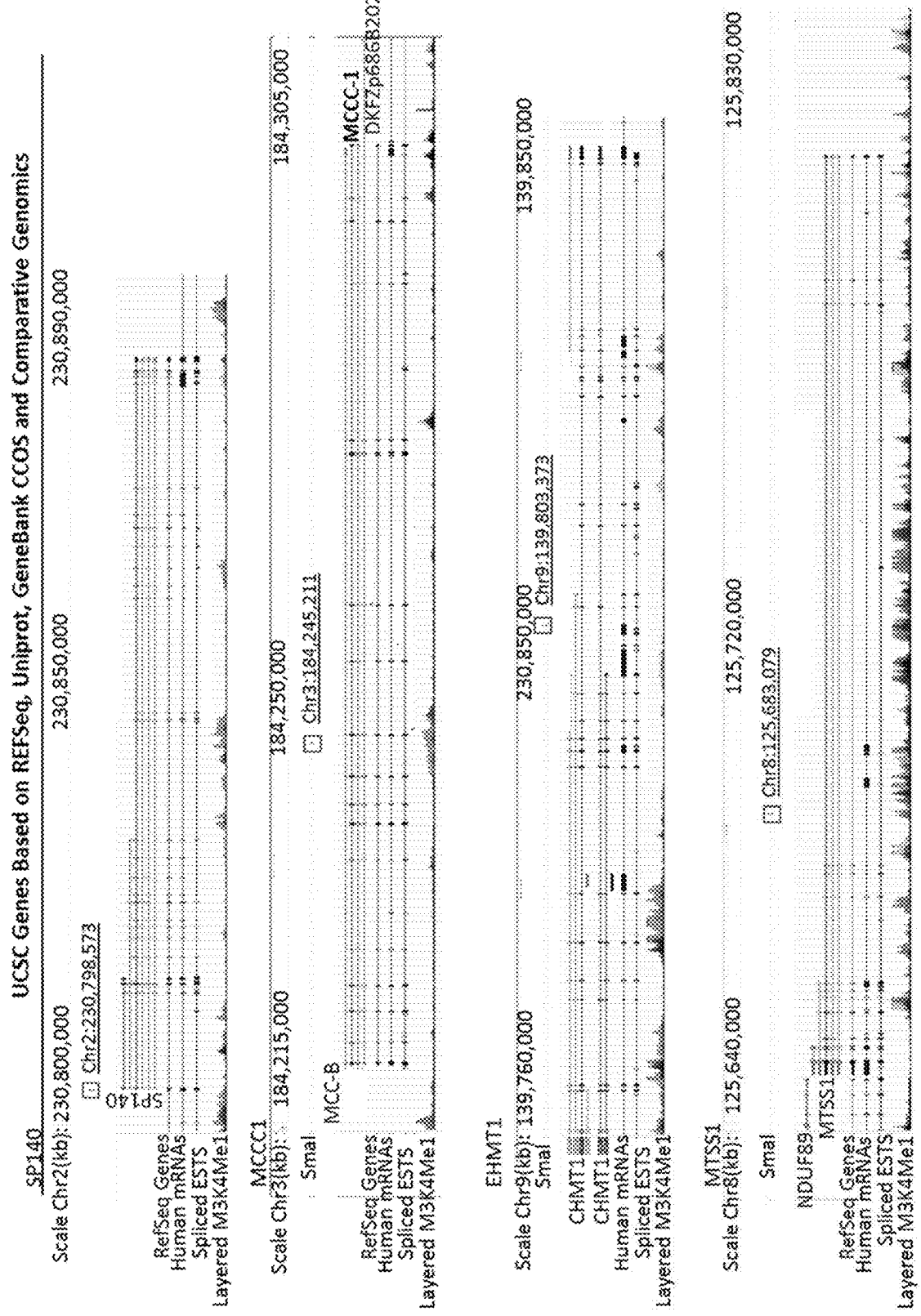
FIG. 27 is an image of the landscape of the specific regions analyzed for these four genes (SP140, MCCC1, EHMT1, and MTSS1) in the human genome.

None of these genes were previously reported as prognostic markers in cancer or leukemias (including AML). For each gene, patients with low DNA methylation levels (below the level of the threshold for each gene of SP140, MCCC1, EHMT1, and MTSS1, defined by the group of low DNA methylation in a test cohortusing defined thresholds roughly equivalent) showed significant longer survival compared to patients with high DNA methylation (Median survival; 14-16 months vs. 22-37 months in the high and low group, respectively, p=0.02-0.001 for each gene) except for EHMT1 (FIG. 25). A classifier was derived where patients with less than 2 genes methylated above thresholds for each gene (SP140, MCCC1, EHMT1, and MTSS1) had even greater significance than single gene measurements (Median survival; 14 months vs. 79+months in 2-4 and 0-1 genes methylated groups, respectively, p=0.0006) (FIG. 26). Furthermore, in multiple regression analysis with other covariates including known AML prognostic factors such as age, cytogenetics and common AML mutations (FLT3, DNMT3a, IDH1, IDH2, RAS, NPM1), it was discovered that the DNA methylation status of these genes is an independent prognostic factor for survival in AML.

These novel biomarkers of outcome in AML may be useful to stratify patients at diagnosis and identify those patients which such poor outcomes that alternate therapies should be sought early on (such as stem cell transplantation). These biomarkers also identify patients with greater benefit from established therapies and thus could be useful adjuncts in precision medicine (personalized therapy). The technology tested (bisulfite-pyrosequencing) is simple and applicable to CLIA approved labs/commercial labs, but similar results would be obtained by other technologies used to measure these particular regions of the genome (for example but not limited to: MSP, qMSP, bis.sequencing, RRBS, probe capture and bisulfite sequencing, methyl-seq etc.).

Example 3: Validation of 4 Loci/CpG Sites

Figure 28:
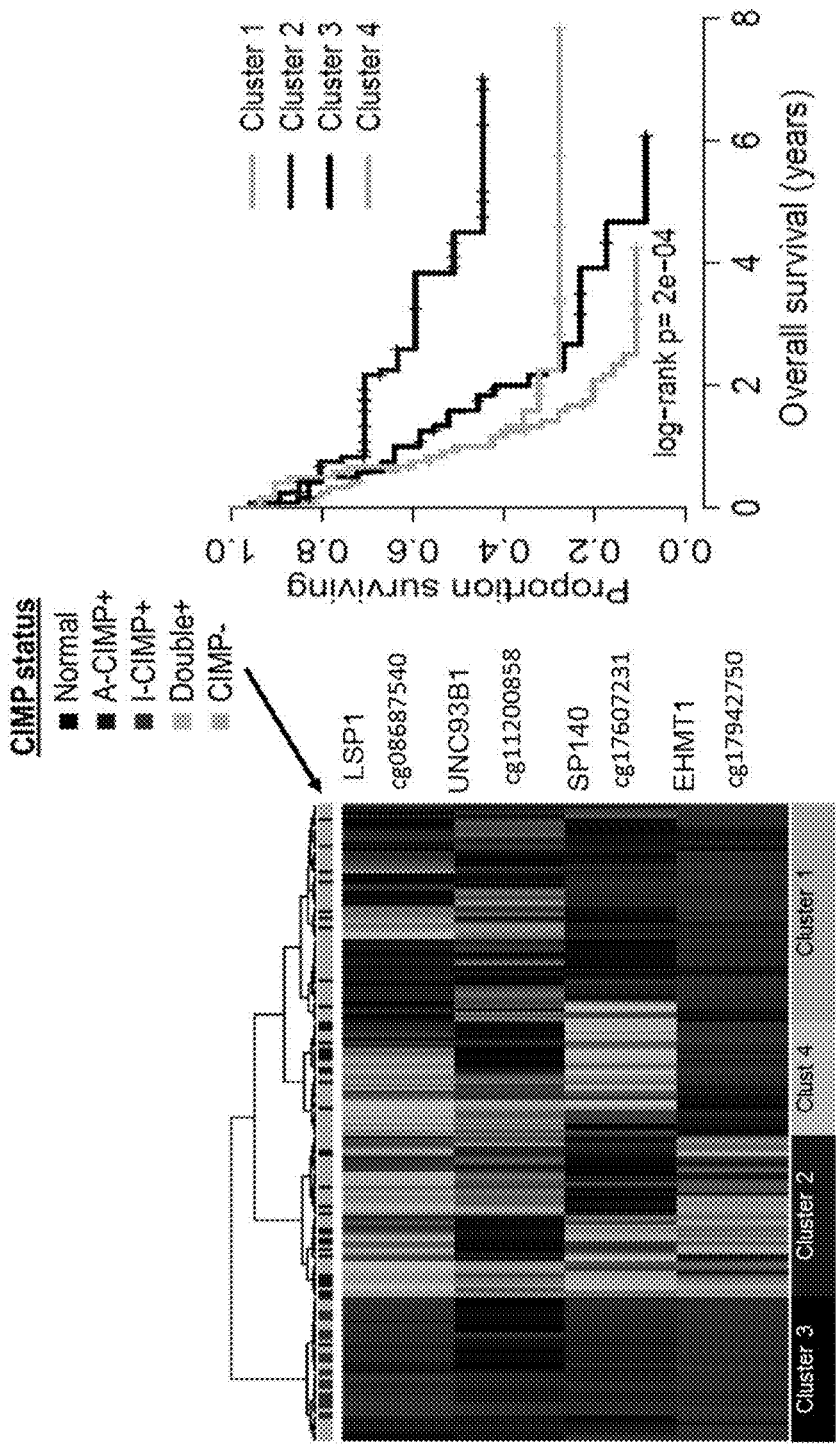
FIG. 28 is an image showing TCGA AML cases clustered on DNA methylation of 4 TET2-DMC sites. Level 1 DNA methylation data were downloaded for 194 AML patients and processed using functional normalization in the mini package in R.

The results presented in FIG. 28 demonstrate that 4 loci/CpG sites were validated. Experiments were designed to use publicly available (TCGA) data generated on a different platform (Illumina Infinium DNA analysis). To run this analysis, DNA has to be treated with sodium bisulfite which changes the sequence of the DNA (C becomes T, except methylated C which remains C). This new sequence (not in nature) is then queried; the persistence of C at CpG sites indicates methylation.

Patients with AML reported on by the TCGA consortium can be classified further based on methylation of these genes. One group (cluster 2 in FIG. 28) had distinct lack of methylation at these loci (green), and this group had the best outcome following chemotherapy (right side graph), validating the original observations. This classification was independent of another DNA methylation process (CIMP or CpG Island Methylator Phenotype).

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of diagnosing and treating a subject having aggressive acute myelogenous leukemia (AML), the method comprising:
   a) determining the level of methylation of a CpG site less than 50 bp upstream of the transcription start site of SP140 in a biological sample of the subject with AML,
   b) comparing the level of methylation of the CpG site with the level of methylation of the CpG site less than 50 bp upstream of the transcription start site of SP140 in normal peripheral blood (NYB),
   c) detecting an increased level of methylation at the CpG site in the sample of the subject with AML as compared to NPB,
   d) diagnosing the subject as having aggressive AML, and
   e) following the diagnosing, administering an alternative therapy to standard chemotherapy to the subject, wherein the alternative therapy is selected from the group consisting of radiation, a bone marrow transplant, a stem cell transplant, and administration of a drug, that reduces DNA methylation levels.

2. The method of claim 1, wherein the level of methylation of the CpG site is measured by a method selected from the group consisting of PCR, methylation-specific PCR, real-time methylation-specific PCR, PCR assay using a methylation DNA-specific binding protein, quantitative PCR, a DNA chip-based assay, pyrosequencing, and bisulfate pyrosequencing.

3. The method of claim 1, wherein the subject is human.

4. A method of treating acute myelogenous leukemia in a subject in need thereof, the method comprising:
   a) determining the level of methylation of SP140 in a biological sample of the subject, b) comparing the level of methylation of SP140 in the sample of the subject with the level of methylation of SP140 in normal peripheral blood (NPB), c) diagnosing the subject as having a form of AML that is likely responsive to treatment with chemotherapy when the level of methylation of SP140 is hypomethylated in the sample of the subject compared with the level of methylation of SP140 in normal peripheral blood (NPB), and d) following the diagnosing, administering chemotherapy to the subject.

5. The method of claim 4, wherein the level of methylation of SP140 is measured by detecting the methylation of CpG sequences in the promoter, gene or related regulatory sequence of SP140.

6. The method of claim 4, wherein the level of methylation of SP140 is measured by a method selected from the group consisting of PM, methylation-specific PCR, real-time methylation-specific PCR, PCR assay using a methylation DNA-specific binding protein, quantitative PCR, DNA chip-based assay, pyrosequencing, and bisulfate pyrosequencing.

7. The method of claim 5, wherein the CpG sequences are located in a region selected from the group consisting of upstream of coding sequences, the promoter sequence, in coding regions, in enhancer regions, in intron regions, and any combination thereof.

8. The method of claim 4, wherein the subject is human.

9. The method of claim 1, wherein a) further comprises determining the level of methylation of at least one CpG site in gene-bodies of each of MCCC1, EHMT1, and MTSS1 in the biological sample of the subject with AML;

wherein b) further comprises comparing the level of methylation of the CpG sites determined in a) with the level of methylation of the same CpG sites in gene-bodies of each of MCCC1, EHMT1, and MTSS1 in normal peripheral blood (NPB); and wherein c) further comprises detecting an increased level of methylation at the at least one CpG site in gene-bodies of each of MCCC1, EHMT1, and MTSS1 in the sample of the subject with AMT as compared to NPB.

* * * * *